US009636305B2

(12) United States Patent
Fathi et al.

(10) Patent No.: US 9,636,305 B2
(45) Date of Patent: May 2, 2017

(54) ANTIEMETIC EXTENDED RELEASE SOLID DOSAGE FORMS

(71) Applicant: RedHill Biopharma Ltd., Tel Aviv (IL)

(72) Inventors: Reza Fathi, HoHoKus, NJ (US); Gilead Raday, Palo Alto, CA (US)

(73) Assignee: RedHill Biopharma Ltd., Tel Aviv (IL)

( * ) Notice: Subject to any disclaimer, the term of this patent is extended or adjusted under 35 U.S.C. 154(b) by 68 days.

(21) Appl. No.: 14/212,694

(22) Filed: Mar. 14, 2014

(65) Prior Publication Data

US 2014/0271887 A1    Sep. 18, 2014

Related U.S. Application Data

(60) Provisional application No. 61/782,395, filed on Mar. 14, 2013.

(51) Int. Cl.
*A61K 9/28* (2006.01)
*A61K 31/4178* (2006.01)
*A61K 9/24* (2006.01)
*A61K 9/20* (2006.01)

(52) U.S. Cl.
CPC .............. *A61K 9/286* (2013.01); *A61K 9/209* (2013.01); *A61K 9/2886* (2013.01); *A61K 31/4178* (2013.01); *A61K 9/2013* (2013.01); *A61K 9/2054* (2013.01); *A61K 9/2846* (2013.01)

(58) Field of Classification Search
None
See application file for complete search history.

(56) References Cited

U.S. PATENT DOCUMENTS

| | | |
|---|---|---|
| 4,720,353 A | 1/1988 | Bell |
| 6,090,411 A | 7/2000 | Pillay et al. |
| 6,500,457 B1 | 12/2002 | Midha et al. |
| 6,517,868 B2 | 2/2003 | Fassihi et al. |
| 6,733,789 B1 | 5/2004 | Stark et al. |
| 6,936,275 B2 | 8/2005 | Fassihi et al. |
| 7,229,642 B2 | 6/2007 | Fassihi et al. |
| 2002/0044962 A1 | 4/2002 | Cherukuri et al. |
| 2002/0071863 A1 | 6/2002 | Dong et al. |
| 2004/0147510 A1 | 7/2004 | Landau et al. |
| 2005/0131045 A1 | 6/2005 | Aronhime et al. |
| 2007/0082857 A1 | 4/2007 | Sawa |
| 2007/0190141 A1 | 8/2007 | Dely |
| 2008/0004260 A1 | 1/2008 | Singh |
| 2008/0044470 A1 | 2/2008 | Petereit et al. |
| 2008/0113021 A1 | 5/2008 | Shen |
| 2008/0200508 A1 | 8/2008 | Rariy et al. |
| 2008/0299197 A1 | 12/2008 | Toneguzzo et al. |
| 2010/0028420 A1 | 2/2010 | Hardy |
| 2010/0196291 A1 | 8/2010 | Halimi |
| 2010/0196472 A1 | 8/2010 | Hirsh et al. |
| 2010/0291208 A1 | 11/2010 | Wang et al. |
| 2011/0003005 A1 | 1/2011 | Venkatesh et al. |
| 2011/0160264 A1 | 6/2011 | Myers et al. |
| 2012/0010213 A1 | 1/2012 | Chandavarkar et al. |
| 2013/0156854 A1 | 6/2013 | Kulkarni et al. |
| 2014/0271851 A1 | 9/2014 | Fathi et al. |

FOREIGN PATENT DOCUMENTS

| | | |
|---|---|---|
| WO | 03/013482 A1 | 2/2003 |
| WO | 03009829 A2 | 2/2003 |
| WO | 2008065424 A1 | 6/2008 |
| WO | 2009/118763 A1 | 10/2009 |

OTHER PUBLICATIONS

Streubel, A. et al. Bimodal drug release achieved with multi-layer matrix tablets: transport mechanisms and device design, Journal of Controlled Release, vol. 69 (2000) pp. 455-468.
Prasad, B. et al. Prospective Trial of Efficacy and Safety of Ondansetron and Fluxoetine in Patients with Obstructive Sleep Apnea Syndrome, Sleep, vol. 33, No. 7, 2010 pp. 982-989.
Recupero, A. Novel Formulations to Improve the Control of Emesis, EURAND Pharmaceutical Technologies Advertorial, Oct. 2010, 1 page.
PCT/IB 14/01633 filed Mar. 14, 2014, International Search Report and the Written Opinion of the International Searching Authority dated Jan. 21, 2015, 17 pages.
Opadry YS-1-7006 Technical Data Sheet (2011).
Venkatesh et al., "Formulation Optimisation of Ondansetron Floating Tablets for Gastric Retention", International Journal of Advanced Pharmaceuticals, 1 (1), 2011, pp. 11-18.
"Using METHOCEL Cellulose Ethers for Controlled Release of Drugs in Hydrophilic Matrix Systems", The Dow Chemical Company, Jul. 2000.
"METHOCEL Cellulose Ethers in Aqueous Systems for Tablet Coating", The Dow Chemical Company, Jul. 2002.
Patka, "Randomized Control Trial of Ondansetron vs. Prochlorperazine in Adults in the Emergency Department", West. J. Emergency. Med., vol. XII, No. 1, Feb. 2011.

(Continued)

*Primary Examiner* — Tigabu Kassa
(74) *Attorney, Agent, or Firm* — Greenberg Traurig, LLP

(57) ABSTRACT

A solid oral dosage form includes a core comprising a non-ionic polymer matrix, a first amount of a first antiemetic drug or a pharmaceutically acceptable salt thereof dispersed within the matrix, and a salt dispersed within the matrix; a first seal coat of a non-ionic polymer matrix surrounding the core; and an immediate release drug layer surrounding the first seal coat, wherein the immediate release drug layer comprises a non-ionic polymer and a second amount of a second antiemetic drug or a pharmaceutically acceptable salt thereof dispersed therein, wherein the drug layer is sufficiently designed to release the second amount of the antiemetic drug over a period of at least 1 hour, wherein the solid oral dosage form is sufficiently designed to release the first amount of the first antiemetic drug and the second amount of the second antiemetic drug over a minimum period of 16 hours.

10 Claims, 11 Drawing Sheets

(56) References Cited

OTHER PUBLICATIONS

Maxton et al., "Selective 5-hydroxytryptamine antagonism: a role in irritable bowel syndrome and functional dyspepsia", Alimentary Pharmacology Therapeutics, 1996, vol. 10, pp. 595-599.

Clayton et al., "The pharmacological properties of the novel selective 5-HT3 receptor antagonist, alosetron and its effects on normal and perturbed small intestinal transit in the fasted rat"; Neurogastroenterology and Motility, Jun. 1999, vol. 11, No. 3, pp. 207-217.

Steadman et al., "Selective 5-Hydroxytryptamine Type 3 Receptor Antagonism with Ondansetron as Treatment for Diarrhea-Predominant Irritable Bowel Syndrome: A Pilot Study"; May Lin Proc, Aug. 1992, vol. 67, pp. 732-738.

Garsed et al., "A randomised trial of ondansetron for the treatment of irritable bowel syndrome with diarrhea", Gut 2013; 0: 1-9.

Pygall et al., "Mechanisms of Drug release in citrate buffered HPMC matrices", International Journal of Pharmaceuticals 2009, 370, pp. 110-120.

ANTIEMETIC EXTENDED RELEASE SOLID DOSAGE FORMS

RELATED APPLICATION

This application claims the benefit of and priority to U.S. provisional Application Ser. No. 61/782,395, filed Mar. 14, 2013, the entire disclosure of which is incorporated by reference in its entirety.

BACKGROUND

The 5-$HT_3$ antagonists are a class of drugs that act as receptor antagonists at the 5-$HT_3$ receptor, a subtype of serotonin receptor found in terminals of the vagus nerve and in certain areas of the brain. With the notable exception of alosetron and cilansetron, which are used in the treatment of irritable bowel syndrome, all 5-$HT_3$ antagonists are antiemetics, used in the prevention and treatment of nausea and vomiting. They are particularly effective in controlling the nausea and vomiting produced by cancer chemotherapy and are considered the gold standard for this purpose. Ondansetron is a serotonin 5-$HT_3$ receptor antagonist used alone or with other medications to prevent nausea and vomiting, and is used for preventing nausea and vomiting caused by cancer drug treatment (chemotherapy) and radiation therapy. It is also used to prevent and treat nausea and vomiting after surgery.

SUMMARY

Extended release solid dosage forms are disclosed herein. More particularly, antiemetic extended release solid dosage forms are disclosed herein for preventing nausea and vomiting. According to aspects illustrated herein, there is disclosed an extended release ondansetron tablet that includes a core comprising a sustained release agent comprising ondansetron, or a pharmaceutically acceptable salt thereof, and an electrolyte; a first seal coating agent; an immediate release drug layer surrounding the first seal coating agent comprising ondansetron, or a pharmaceutically acceptable salt thereof; and a second seal coating agent, wherein the immediate release layer is sufficiently designed to release about ¼ of a total dose of ondansetron within about 1 hour after oral administration, and wherein the core is sufficiently designed to release the remaining dose of ondansetron for a period of up to 24-hours via zero-order release. In an embodiment, the core comprises about 18 mg of ondansetron free base. In an embodiment, the core comprises about 20 mg of ondansetron free base. In an embodiment, the core comprises about 28 mg of ondansetron free base. In an embodiment, the electrolyte is sodium dihydrogen citrate anhydrous present at a concentration in the range of about 50% to about 100% by weight of the sustained release agent. In an embodiment, the sustained release agent is a hydrophilic swellable matrix. In an embodiment, the hydrophilic swellable matrix of the core is METHOCEL™ K4M Premium DC, the hypromellose of the first seal coating and the second seal coating is METHOCEL™ E5 Premium LV, and the hypromellose of the immediate release drug layer is METHOCEL™ E5 Premium LV. In an embodiment, the hydrophilic swellable matrix of the core is METHOCEL™ K4M Premium CR, the hypromellose of the first seal coating and the second seal coating is METHOCEL™ E5 Premium LV, and the hypromellose of the immediate release drug layer is METHOCEL™ E5 Premium LV. In an embodiment, the immediate release layer comprises about 6 mg of ondansetron.

According to aspects illustrated herein, there is disclosed an extended release ondansetron tablet that includes a core comprising a hydrophilic swellable matrix comprising ondansetron, or a pharmaceutically acceptable salt thereof, and sodium dihydrogen citrate anhydrous; a first seal coating comprising hypromellose and plasACRYL™; an immediate release drug layer surrounding the first seal coating comprising ondansetron, or a pharmaceutically acceptable salt thereof, hypromellose and plasACRYL™; and a second seal coating comprising hypromellose and plasACRYL™ T20, wherein the immediate release layer is sufficiently designed to release about ¼ of a total dose of ondansetron within about 1 hour after oral administration, and wherein the core is sufficiently designed to release the remaining dose of ondansetron for a period of up to 24-hours via zero-order release. In an embodiment, the core comprises about 18 mg of ondansetron free base. In an embodiment, the core comprises about 20 mg of ondansetron free base. In an embodiment, the core comprises about 28 mg of ondansetron free base. In an embodiment, the sodium citrate anhydrous is present at a concentration in the range of about 50% to about 100% by weight of the hydrophilic swellable matrix. In an embodiment, the hydrophilic swellable matrix of the core is METHOCEL™ K4M Premium DC, the hypromellose of the first seal coating and the second seal coating is METHOCEL™ E5 Premium LV, and the hypromellose of the immediate release drug layer is METHOCEL™ E5 Premium LV. In an embodiment, the hydrophilic swellable matrix of the core is METHOCEL™ K4M Premium CR, the hypromellose of the first seal coating and the second seal coating is METHOCEL™ E5 Premium LV, and the hypromellose of the immediate release drug layer is METHOCEL™ E5 Premium LV. In an embodiment, the immediate release layer comprises about 6 mg of ondansetron.

According to aspects illustrated herein, there is disclosed an extended release solid dosage form that includes an internal portion, wherein the internal portion comprises a first dose of at least one serotonin antagonist; a first coating, wherein the first coating directly encapsulates the internal portion of the solid dosage form; a drug layer coating, wherein the drug layer coating directly encapsulates the first coating, wherein the drug layer coating comprises a second dose of the at least one serotonin antagonist, wherein the drug layer coating is at least 4%, by weight, of the solid dosage form, wherein the second dose is equal to at least 15%, by weight, of a total dose of the at least one serotonin antagonist in the solid dosage form, and wherein the first dose is equal to the total dose minus the second dose; and a second coating, wherein the second coating directly encapsulates the drug layer coating, wherein the internal portion has solubility in water of X, wherein the first coating, the drug layer coating, and the second coating have solubility in water of at least Y, and wherein X is less than Y. In an embodiment, the at least one serotonin-3 receptor antagonist is ondansetron hydrochloride. In an embodiment, the second dose is equal to at least 20%, by weight, of the total dose of the at least one serotonin-3 receptor antagonist in the solid dosage form. In an embodiment, the at least one serotonin-3 receptor antagonist is ondansetron hydrochloride. In an embodiment, the second dose is equal to at least 25%, by weight, of the total dose of the at least one serotonin-3 receptor antagonist in the solid dosage form. In an embodiment, the first coating and the second coating comprise a hydrophilic material. In an embodiment, the drug layer further comprises a hydrophilic material. In an embodiment, the hydrophilic material is hypromellose. In an embodiment, the first coating and the second coating are each of at least 1.5%, by weight, of the solid dosage form. In an embodiment, the ratio of the hypromellose to the at least one serotonin-3 receptor antagonist in the drug layer is about 4:6. In an embodiment, a total amount of hypromellose in the first coating, the drug layer, and the second coating is less than 4%, by weight, of the solid dosage form. In an embodiment, the core further comprises sodium citrate in an amount of less than 15%, by weight, of the core. In an embodiment, X is sufficiently less than Y so that the second dose is substantially released from the solid dosage form within less than 12 hours after the solid dosage form is exposed to an aqueous environment, and the first dose is substantially released from the solid dosage in a zero-order release profile over a period of 12 to 24 hours after the solid dosage form is exposed to the aqueous environment. In an embodiment, the aqueous environment has a pH in the range of pH 1.5 to pH 7.5. In an embodiment, the solid dosage form is compressed into a tablet. In an embodiment, the solid dosage form is formed as a capsule. In an embodiment, the core further comprises glycine in an amount of less than 20%, by weight, of the core.

According to aspects illustrated herein, there is disclosed an extended release ondansetron tablet made by compressing a sustained release core tablet and then coating the core tablet with a first seal coat followed by drug coat and finally a second seal coat, wherein the core tablet comprises a hydrophilic swellable matrix comprising ondansetron hydrochloride and sodium dihydrogen citrate anhydrous, wherein the first seal coat comprises comprising hypromellose and plasACRYL™, wherein the drug coat comprises ondansetron hydrochloride, hypromellose and plasACRYL™, and wherein the second seal coat comprises hypromellose and plasACRYL™ T20.

According to aspects illustrated herein, there is disclosed a solid oral dosage form that includes a core comprising a non-ionic polymer matrix, a first amount of a first antiemetic drug or a pharmaceutically acceptable salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of a second antiemetic drug or a pharmaceutically acceptable salt thereof dispersed therein, wherein the drug layer is sufficiently designed to release the second amount of the antiemetic drug over a period of at least 1 hour, wherein the solid oral dosage form is sufficiently designed to release the first amount of the first antiemetic drug and the second amount of the second antiemetic drug over a minimum period of 16 hours.

According to aspects illustrated herein, there is disclosed a solid oral dosage form that includes a core comprising hypromellose, 18 mg of ondansetron or an equivalent amount of an ondansetron salt thereof, and sodium citrate anhydrous; a first seal coat surrounding the core and comprising hypromellose; and an immediate release drug layer surrounding the first seal coat and comprising hypromellose and 6 mg of ondansetron or an equivalent amount of an ondansetron salt thereof, the immediate release drug layer sufficient to release the ondansetron over a period of at least 1 hour, wherein the total amount of ondansetron in the dosage form is released over 24 hours.

According to aspects illustrated herein, there is disclosed a solid oral dosage form that includes a core comprising a non-ionic polymer matrix, a first amount of ondansetron or an equivalent amount of an ondansetron salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of ondansetron or an equivalent amount of an ondansetron salt thereof dispersed therein, wherein the solid oral dosage form results in an in vitro ondansetron dissolution profile when measured in a type 2 paddle dissolution apparatus at 37° C. in aqueous solution containing distilled water at 50 rpm that exhibits: a) from about 20% to 50% of the total ondansetron is released after two and a half hours of measurement in the apparatus; b) from about 50% to 70% of the total ondansetron is released after five hours of measurement in the apparatus; and c) no less than about 90% of the total ondansetron is released after fifteen hours of measurement in the apparatus.

According to aspects illustrated herein, there is disclosed a packaged pharmaceutical preparation that includes a plurality of the solid oral dosage forms of the present invention in a sealed container and instructions for administering the dosage forms orally to effect prevention of nausea and vomiting According to aspects illustrated herein, there is disclosed a pharmaceutical preparation that includes a plurality of the solid oral dosage forms of the present invention each in a discrete sealed housing, and instructions for administering the dosage forms orally to effect prevention of nausea and vomiting.

According to aspects illustrated herein, there is disclosed a method for controlling nausea and vomiting comprising administering a solid dosage form of the present invention to a patient, wherein nausea and vomiting are controlled after an amount of ondansetron has been released from the solid dosage form, reaches the systemic circulation of the patient, and is absorbed by the patient.

According to aspects illustrated herein, there is disclosed a method for reducing side effects of chemotherapy treatment comprising administering a solid dosage form of the present invention to a patient, wherein side effects including nausea and vomiting are reduced after an amount of ondansetron has been released from the solid dosage form, is absorbed by the patient, and reaches the systemic circulation of the patient.

According to aspects illustrated herein, there is disclosed a method for reducing side effects of motion sickness comprising administering a solid dosage form of the present invention to a patient, wherein side effects including nausea and vomiting are reduced after an amount of ondansetron has been released from the solid dosage form, is absorbed by the patient, and reaches the systemic circulation of the patient.

According to aspects illustrated herein, there is disclosed a method for reducing side effects of anesthetics comprising administering a solid dosage form of the present invention to a patient after the patient has been exposed to an anesthetic, wherein side effects including nausea and vomiting are reduced after an amount of ondansetron has been released from the solid dosage form, is absorbed by the patient, and reaches the systemic circulation of the patient.

BRIEF DESCRIPTION OF THE DRAWINGS

The presently disclosed embodiments will be further explained with reference to the attached drawings. The drawings shown are not necessarily to scale, with emphasis instead generally being placed upon illustrating the principles of the presently disclosed embodiments.

Figure 1:
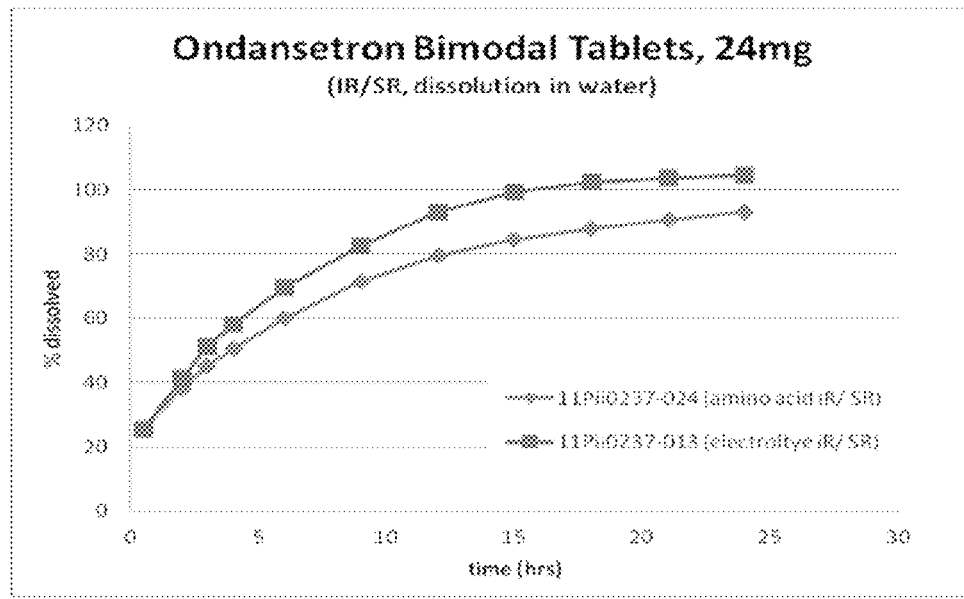
FIG. 1 illustrates the dissolution profiles of ondansetron from two embodiments of extended release solid dosage forms of the present disclosure as measured using a USP type 2 (paddle) dissolution system at 50 rpm, at a temperature of 37±0.5° with distilled water as a dissolution medium.

While the above-identified drawings set forth presently disclosed embodiments, other embodiments are also contemplated, as noted in the discussion. This disclosure presents illustrative embodiments by way of representation and not limitation. Numerous other modifications and embodiments can be devised by those skilled in the art which fall within the scope and spirit of the principles of the presently disclosed embodiments.

DETAILED DESCRIPTION

As used herein the following terms have the definitions set forth below.

"Hydropathy" refers to a scale of solubility characteristics combining hydrophobicity and hydrophilicity of amino acids. More particularly this term refers to a sliding scale, similar to a pH scale, which assigns relative values which represent the relative balance between hydrophobic and hydrophilic components of an amino acid. A typical scale is set forth in Pliska et al., J. Chromatog. 216, 79, 1981, entitled Relative Hydrophobic Character of Amino Acid Side Chains, wherein glycine has a value of 0, representing a relatively equal balance between hydrophobic and hydrophilic components and may be referred to as relatively 'neutral', 'balanced', 'slightly hydrophilic'; or 'weakly hydrophobic', iso-leucine has a positive value of 1.83 and is strongly hydrophobic, and on the opposite end of the scale, aspartic acid has a negative value of −2.15 and may be characterized as strongly hydrophilic. Such a scale and the hydropathy characteristics described herein are well known and understood by those skilled in the art.

"Monolithic" refers to tablets that do not require multiple layers, special shapes, osmotic compartments and/or specialized coatings, typically without joints or seams, and are capable of being tableted on modern high speed tableting equipment.

The term "bimodal" as used herein refers to bimodal drug release profiles (fast release/slow release).

A "serotonin antagonist" or "5-HT$_3$ receptor antagonist" refers to a class of medications useful in preventing and relieving nausea and vomiting caused by chemotherapy and anesthesia. It is believed that serotonin antagonists work by blocking the effects of the chemical serotonin, which is produced in the brain and the stomach. 5-HT$_3$ receptor antagonists efficacious in treating chemotherapy-induced emesis include, but are not limited to, dolasetron, granisetron, ondansetron, palonosetron, tropisetron.

Extended release solid dosage forms are provided. More particularly, the present disclosure relates to extended release bimodal solid dosage forms for the prevention of chemotherapy induced nausea and vomiting. In an embodiment, an extended release solid dosage form includes an internal portion, wherein the internal portion comprises a first dose of ondansetron; a first coating, wherein the first coating directly encapsulates the internal portion of the solid dosage form; a drug layer coating, wherein the drug layer coating directly encapsulates the first coating, wherein the drug layer coating comprises a second dose of ondansetron, wherein the drug layer coating is at least 4%, by weight, of the solid dosage form, wherein the second dose is equal to at least 15%, by weight, of a total dose of the ondansetron in the solid dosage form, and wherein the first dose is equal to the total dose minus the second dose; and a second coating, wherein the second coating directly encapsulates the drug layer coating, wherein the internal portion has solubility in water of X, wherein the first coating, the drug layer coating, and the second coating have solubility in water of at least Y, and wherein X is less than Y. In an embodiment, the extended release solid dosage form is capable of producing a burst of approximately 25% ondansetron, followed by a zero-order release of the remaining ondansetron over a period of between 16-20 hours. In an embodiment, the extended release solid dosage form is capable of producing a burst of approximately 25% ondansetron, followed by a zero-order release of the remaining ondansetron over a period of between 20-30 hours.

In an embodiment, a solid dosage form of the present invention includes oral dosage forms such as tablets, capsules, caplets, granules. In an embodiment, a solid dosage form of the present invention is a rectal dosage form such as suppository.

Ondansetron

Ondansetron is an effective antiemetic agent that has greatly improved the quality of life of patients undergoing chemotherapy. The usual dose administered to patients ranges between 8 mg, 16 mg, 24 mg or 32 mg per day, administered once a day or in divided doses. Ondansetron displays central and/or peripheral action by preferentially blocking the serotonin $5-HT_3$ receptors. Ondansetron hydrochloride (HCl) is the dihydrate, the racemic form of ondansetron. Ondansetron has the empirical formula C18H19N3O.HCl.2H2O, representing a molecular weight of 365.9. Ondansetron HCl dihydrate is a white to off-white powder that is soluble in water and normal saline.

Internal Portion ("Core") of Solid Dosage Forms of an Embodiment of the Present Disclosure As a tablet passes through the human digestive tract, it is subjected to pH values ranging from about 1.5 to about 7.4. The saliva of the mouth has a neutral pH, the stomach has a pH varying from about 1.5-4.0, and the pH of the intestines carries a pH between about 5.0-7.5. For a drug to approach zero-order release, the drug's dissolution must be independent of the pH in the surrounding environment. The internal portion ("core") of a dosage form of the present disclosure may approach zero order delivery of a drug.

Internal Portion—Electrolyte Platform

In an embodiment, the internal portion ("core") is comprised of a hydrophilic swellable matrix, in which is disposed a pharmaceutically active agent ("API") and one or more electrolytes. The "electrolyte core" is a slow release ("SR") formulation. The one or more electrolytes, either in combination with the API or another salt upon reaction in an aqueous medium, causes a hardening reaction of the matrix. The rate of outward diffusion is controlled by exposing the internal portion to an aqueous medium. This in turn causes a hardening reaction to occur in a time dependent manner from the outer boundaries towards the inner boundaries of the internal portion; the hardened reaction product, in turn limits outward diffusion of the API as the inward ingress of aqueous medium causes a progressive hardening from the outer boundaries of the internal portion in a direction towards the inner core there.

The internal portion employs the colloidal chemistry phenomenon of "salting-out" to moderate the swelling and erosion kinetics of a non-ionic polymer matrix containing the API and one or more electrolytes. The presence of these electrolytic compounds in the form of ionizable salts allows for non-collapsible diffusion channels to form; channelization agents used in the past were not ionizable, therefore, the diffusion channels were unpredictable leading to poor release profiles and lack of control. The electrolytes also contribute to a contracting micro-environment within the tablet, whose pH is mediated by the pKa of the electrolyte, thus either enhancing or suppressing the solubility of the API itself. As the matrix hydrates, the electrolytes and polymer compete for water of hydration with the API, resulting in a programmable rate of release. The internal portion is thus capable of zero-order, pH-independent release of an API for up to 24-hours, without regard to the solubility of the API itself.

Through processes of ionic interaction/complexation/molecular and/or self association between a drug and an electrolyte or electrolyte/drug combinations, homogeneously dispersed in a swellable polymer such as hydroxypropylmethylcellulose (HPMC), modify the dynamics of the matrix swelling rate and erosion of the swellable polymer, in accordance with variations in an external pH environment ranging from about 1.5-7.0. These interactions result in controlled matrix hardening. Such hardening is responsible for the control of polymer erosion/dissolution and drug release rates. By design, solvent penetrates the periphery of the tablet and a rapid initial interaction between drug and electrolyte embedded in the polymeric matrix causes immediate hardening of the outer tablet boundary, the rate of hardening consistently decreases toward the center of the matrix core in a time-dependent manner over a long period of time (e.g. 24 hours).

The differential rate of matrix hardening is the driving principle in the internal portion, which is dependent on and controlled by the rate of liquid ingress to the internal portion core. With the simultaneous time-dependent decrease in gel layer integrity, the rate of drug diffusion decreases. This phenomenon compensates for the increase in diffusion path length and decrease in the surface area of the receding core which arises from the swelling property of the polymer. Hence, better controlled, preferably zero order, drug release is achieved. The drug release process can be tailored for up to 24 hours. Control of the changes in core hardness and synchronization of the rubbery/swelling front and described receding phase boundaries as well as erosion of the dissolution front boundary (i.e. erosion of the tablet periphery) results in controlled drug release, preferably including zero order kinetics. Optionally, polymer matrix hardenings is also easily achievable through double salt interaction. This binary salt combination is also uniformly dispersed in the polymeric matrix, which through ionic interaction/complexation/molecular and/or self association, increases the relative strength and rigidity of the matrix, resulting in controlled drug release with a similar mechanism to that described above.

One hydrophilic matrix material useful in the internal portion is HPMC K4M. This is a nonionic swellable hydrophillic polymer manufactured by "The Dow Chemical Company" under the tradename "Methocel". HPMC K4M is also abbreviated as HPMC K4MP, in which the "P" refers to premium cellulose ether designed for controlled release formulations. The "4" in the abbreviation suggests that the polymer has a nominal viscosity (2% in water) of 4000. The percent of methoxyl and hydroxypropyl groups are 19-24 and 7-12, respectively. In its physical form, HPMC K4M is a free-flowing, off-white powder with a particle size limitation of 90%<100 mesh screen. There are other types of HPMC such as K100LVP, K15MP, K100MP, E4MP and E10MP CR with nominal viscosities of 100, 1500, 100000, 4000, and 10000 respectively.

Because the internal portion consists of a non-covalently bonded matrix, the manufacturing process is a fundamentally two-step process of dry-blending and direct compression.

In an embodiment, a salt is dispersed in the matrix at a concentration in the range of about 50% to about 100% by weight of the polymeric matrix. In an embodiment, the salt is selected from one or two members of the group consisting of sodium chloride, sodium bicarbonate, potassium bicarbonate, sodium citrate, sodium bisulfate, sodium sulfite, magnesium sulfate, calcium chloride, potassium chloride, and sodium carbonate.

It is believed that an interaction between drug and salt forms a complex in the surrounding swellable matrix in a layered fashion because it occurs in a time-dependent manner as the solvent media for drug release penetrates the tablet inwardly. Likewise, because the catalyst for the initiation of drug release is liquid ingress, so too is the rate of drug release controlled by the inwardly progressive hardening of the salt complex.

A binary salt system (e.g. calcium chloride and sodium carbonate) may also be used in which case the hardening reaction may be a function of interaction between the salts. Calcium chloride may be incorporated to form a complex with sodium carbonate. With this combination, the reaction products are insoluble calcium carbonate and soluble channel former, sodium chloride. Hence the calcium carbonate embeds itself in the polymer matrix, initiates hardening and slowly dissolves with liquid ingress and the subsequent creation of diffusion channels as drug diffuses out. In a similar way, other binary salt combinations display time-dependent "hardening/de-hardening" behavior.

The amount of salt to be used may be determined taking into consideration the solubility of the drug, the nature of the polymer and the required degree of matrix hardening desired. In case of diltiazem hydrochloride in a HPMC matrix, 100 mg of sodium bicarbonate provides suitable matrix hardening for zero order controlled release, while in the case of the same amount of drug in a different polymer such as polyethylene oxide, 50 mg of sodium bicarbonate appears to be ideal for the attainment of controlled zero order release.

The pharmaceutically active ingredient can be selected from the group consisting of Aprepitant (Emend), Dexamethasone, Dolasetron (Anzemet), Dronabinol (Marinol), Droperidol (Insapsine), Granisetron (Kytril), Haloperidol (Haldol), Methylprednisolone (Medrol), Metoclopramide (Reglan), Nabilone (Cesamet), Ondansetron (Zofran), Palonosetron (Aloxi), Prochlorperazine (Procomp), and pharmaceutically acceptable salts thereof, or combinations thereof.

In an embodiment, the internal portion of a solid dosage form of the present disclosure is a hydrophilic swellable polymeric matrix having dispersed within the matrix a pharmaceutically effective amount of at least one serotonin antagonist whose degree of solubilization is substantially independent of pH over a pH in the range of pH 1.5 to pH 7.5 and an inorganic salt, wherein the inorganic salt is present at a concentration in the range of 50% to 100% by weight of the polymeric matrix. In an embodiment, the inorganic salt is sodium citrate. In an embodiment, the hydrophilic swellable polymeric matrix is hydroxypropylmethylcellulose or polyethylene oxide.

An internal portion as described above can be prepared by a process as disclosed in U.S. Pat. No. 6,090,411, which is incorporated herein by reference for the teachings disclosed therein.

Internal Portion—Amino Acid Platform

In an embodiment, the internal portion ("core") is comprised of a hydrophilic extragranular polymer in which is dispersed a plurality of granules of an API, granulated with at least one amino acid, and an intragranular polymer. The "amino acid core" or "AA core" is a slow release ("SR") formulation. The granules are dispersed within a hydrophilic extragranular polymer to form a monolithic matrix. The extragranular polymer more rapidly hydrates relative to the intragranular polymer. The rapid hydration of the extragranular polymer assists in the approximation of a linear release profile of the drug and facilitates near 100% dissolution, while extending the duration of release and reducing the burst effect frequently encountered with extended release dosage forms. Although the linear release rate can be tailored to fit the needs of each application by selecting polymers for different dissolution rates, as understood by one of ordinary skill in the art, a release time of 12 to 24 hours is most preferred.

The intragranular polymer is combined with an API, and at least one amino acid to form granules. The intragranular polymer may be one or more of the following: polyvinyl acetate, a galactomannan polysaccharide such as hydroxypropyl guar, guar gum, locust bean gum, pectin, gum acacia, gum tragacanth, karaya gum, cellulose ethers such as hydroxyproplymethyl cellulose (HPMC), as well as other gums and cellulose ethers to be chosen by one of skill in the art for properties consistent with the teaching of this invention. In an embodiment, the intragranular polymer is a galactomannan polysaccharide such as guar gum (with a viscosity range of 75-6000 cps for a 1% solution at 25° C. in water and a particle size 10-300 µm).

The intragranular polymer in the internal portion is present in amounts between 4% and 45% of the total dosage form weight. The specific type of intragranular polymer and amount of intragranular polymer used is chosen depending on the desired rate of drug release, viscosity of the polymer, the desired drug load, and the drug solubility. The intragranular polymer hydrates less rapidly than the extragranular polymer. The relative difference in hydration rates between the two polymers creates a less viscous intragranular polymer and a more viscous extragranular polymer. Over time, the difference in viscosity contributes to the continuous erosion and disintegration of the solid dosage form.

Amino acids are useful in this embodiment for two primary reasons. First, the amino acids are a factor in determining the viscosity of the polymers. As noted above, over time the difference in viscosity between the extragranular and intragranular polymers contributes to the continuous erosion and disintegration of the core, facilitating about 100% release of the drug. Another important aspect of using an amino acid in the granule is that the hydropathy of the amino acid may be exploited to modulate the solubility and release of a drug.

Thus, the amino acid is selected for hydropathy characteristics depending on the solubility characteristics of the active compound. When the compound is at least sparingly water soluble, that is, for example, sparingly soluble, soluble or has a higher level of solubility, as defined by the United States Pharmacopeia, an amino acid is utilized which has a relatively equal balance between hydrophilic and hydrophobic components, i.e. is neutral or balanced or within close proximity to neutrality, or is relatively more strongly hydrophilic.

For example, dissolution and release of soluble or sparingly soluble ionizable drugs such as verapamil HCl can be controlled by the inclusion of one or more amino acids in the granules. Without subscribing to a particular theory of drug release and dissolution, it is believed that the nature of the granulation process is such that as the formulation components come into close molecular contact, granulation reduces the available surface area of the particles, thus reducing the initial rate of hydration. In the granulated formulations, there is sufficient time for the amino acid carboxyl (COOH—) groups and amino groups ($NH_2/NH_{3+}$) to interact with hydroxyl groups on the polymer, thus mediating the swelling, viscosity, and gel properties of the polymer and thereby exerting control on the swelling mediated drug diffusion. Simultaneously, the amino acid carboxyl groups may also interact with suitable polar substituents on the drug molecule such as secondary or tertiary amines. Furthermore, the hydrophilic and ionic nature of amino acids results in their extensive hydration in aqueous solution. Consequently, the amino acid promotes erosion, but also competes with both the polymer and the drug for water uptake necessary for hydration and dissolution.

However, when the active compound is less than sparingly soluble, including active compounds which are slightly soluble to insoluble, a combination of at least two amino acids is utilized, one of which is strongly hydrophobic, the other of which is relatively more hydrophilic than the hydrophobic component, that is, about neutral or balanced to strongly hydrophilic.

The amino acid component of the granules may comprise any pharmaceutically acceptable α-amino or β-amino acids, salts of α- or β-amino acids, or any combination thereof. Examples of suitable α-amino acids are glycine, alanine, valine, leucine, iso-leucine, phenylalanine, proline, aspartic acid, glutamic acid, lysine, arginine, histidine, serine, threonine, cysteine, asparagine, and glutamine. An example of a β-amino acid is β-alanine.

The type of amino acids used in this embodiment of the internal portion can be described as hydrophilic, hydrophobic, salts of hydrophilic or hydrophobic amino acids, or any combination thereof. Suitable hydrophobic amino acids for use include, but are not limited to, iso-leucine, phenylalanine, leucine, and valine. Further, hydrophilic amino acids, such as glycine, aspartate and glutamate can be used in the granule. Ultimately, any amino acid, and any amino acid in combination with another amino acid, can be employed in the present invention to enhance the solubility of a drug. For a detailed list of amino acids that can be used in the present invention and the hydropathy of each, see Albert L. Lehninger et al., Principles of Biochemistry 113 (2nd ed. Worth Publishers 1993).

The type and amount of amino acid may be chosen depending on the desired drug load, desired rate of drug release, and the solubility of the drug. The amino acid in the dosage form is typically between 4% and 45% of the total dosage form weight. However, the amount of amino acid is preferably between 11% and 29% by weight of the total dosage form.

The granules may optionally be blended with a coating material, for example magnesium stearate or other hydrophobic derivatives of stearic acid. The amount of coating material used can vary from 1% to 3% of the total weight of the dosage form. Normally, magnesium stearate is used to facilitate processing, for example as a flow aid, but in the present invention magnesium stearate has the additional benefit of retarding dissolution, due to the hydrophobic nature of the coating material. Therefore, magnesium stearate can be used to further adjust the solubility of the dosage form and further retard drug release from the granules.

To enhance the mechanical properties and/or to influence the drug release rate further, the granules may also contain small amounts of inert pharmaceutical fillers and binders/granulating agents as is conventional to the art. Examples of inert pharmaceutical fillers include: lactose, sucrose, maltose, maltodextrins, dextrins, starch, microcrystalline cellulose, fructose, sorbitol, di- and tri-calcium phosphate. Examples of granulating agents/binders include starch, methylcellulose, hydroxy propyl- or hydroxypropylmethyl cellulose, sodium carboxymethyl cellulose, or poly-vinyl pyrrolidone, gum acacia tragacanth and sucrose. Other suitable fillers may also be employed as understood by one of skill in the art. Depending on the physical and/or chemical properties of the drug, a wet granulation procedure (using either an aqueous or organic granulating fluid) or a dry granulation procedure (e.g. slugging or roller compaction) can be employed.

After the granulation of the pharmaceutically active compound, intragranular polymer, amino acids, and optionally fillers and hydrophobic coating materials, the granule is then blended with and dispersed within an extragranular polymer.

The extragranular polymer may be one or more of the following: polyethylene oxide, a galactomannan polysaccharide such as hydroxypropyl guar, guar gum, locust bean gum, pectin, gum acacia, gum tragacanth, karaya gum, cellulose ethers such as hydroxypropylmethyl cellulose (HPMC), as well as other gums and cellulose ethers to be chosen by one of skill in the art for properties consistent with the teaching of this invention. The extragranular polymer may be a galactomannan polysaccharide such as guar gum (with a viscosity range of 75-6000 cps for a 1% solution at 25° C. in water and a particle size 10-300 μm). As noted above the extragranular polymer should hydrate rapidly and achieve a high level of viscosity in a shorter period of time relative to the intragranular polymer.

The difference in hydration rates between the extragranular polymer and intragranular polymer is achieved by three principle means, (1) by choosing polymers based on differences in particle size, (2) by choosing polymers based on differences in molecular weight and chemical composition and (3) by choosing polymers based on a combination of (1) and (2). Although this disclosure focuses primarily on polymers chosen for differences in particle size, it is possible to achieve the results of this invention by using an intragranular polymer with a different molecular weight and/or chemical composition than the extragranular polymer. For example, polyethylene oxide may be used as the intragranular polymer and guar gum as the extragranular polymer.

Particle size is another characteristic of commercial guar gum because coarser particles ensure rapid dispersion, while finer particles are ideal for fast hydration. Therefore, in order to achieve the desired result of the present invention. In an embodiment, the finer particles are used for the extragranular polymer and less fine particles are used for the intragranular polymer particles. The brochure by HERCULES Incorporated, entitled "Supercol® Guar Gum, 1997" contains the typical properties of guar gum of different grades and particles sizes. Other rapidly hydrating extragranular polymers which may be used include: polyethylene oxide (PEO), cellulose ethers and polysaccharides such as hydroxypropyl guar, pectin, gum acacia and tragacanth, karaya gum, mixtures of the aforementioned polymers and any other polymers to be chosen by one of skill in the art for properties consistent with the teaching of this invention. The amounts and the types of extragranular polymer are chosen depending on the desired drug load, rate of drug release and drug solubility. A range of about 4-47% (by total tablet weight) of extragranular polymer has been found to be feasible, but a range of about 15%-47% is particularly preferred.

A therapeutic amount of an API, for example up to about 75% of the total dosage form weight, can be included in the internal portion. With this drug load, the internal portion approximates a linear release profile, with a minimal, or elimination of, burst effect. However, if desired by a skilled artisan, the extragranular polymer may contain additional amounts of the pharmaceutically active compound to achieve more rapid drug release or an induced burst effect, as well as contain amino acids to mediate dissolution of the pharmaceutically active compound, as described above.

The tableted oral extended release dosage form optionally may be coated with polymers, plasticizers, opacifiers, and colourants as is conventional in the art.

In an embodiment, the internal portion of a solid dosage form of the present disclosure is (1) a plurality of granules comprising (a) at least one serotonin antagonist; (b) at least one amino acid; and (c) an intragranular polymer; the intragranular polymer comprising 4% to 45% of the total dosage form by weight and, (2) a hydrophilic extragranular polymer in which the granules are dispersed, the extragranular polymer comprising 4% to 47% of the total dosage form by weight and being more rapidly hydrating than the intragranular polymer, wherein the amino acid is selected for hydropathy characteristics depending on solubility characteristics of the at least one serotonin antagonist and comprises 11% to 29% of the total dosage form by weight. In an embodiment, when the at least one serotonin antagonist is at least sparingly soluble in water, the amino acid has a relatively equal balance between hydrophobic and hydrophilic components or is relatively more hydrophilic In an embodiment, when the at least one serotonin antagonist is less than sparingly soluble in water, the amino acid is a combination of at least two amino acids, one of which is moderately or strongly hydrophobic, the other of which is relatively more hydrophilic. In an embodiment, the intragranular polymer comprises at least one of the following: polyvinyl acetate, a galactomannan polysaccharide selected from the group consisting of hydroxypropyl guar, guar gum, locust bean gum, pectin, gum acacia, tragacanth, karaya gum, or cellulose ethers. In an embodiment, the amino acid is selected from the group consisting of: a) α-amino acids b) β-amino acids c) a combination of α- and β-amino acids. In an embodiment, the α-amino acid is at least one member selected from the group consisting of glycine, alanine, valine, leucine, iso-leucine, phenylalanine, proline, aspartic acid, glutamic acid, lysine, arginine, histidine, serine, threonine, cysteine, asparagine and glutamine. In an embodiment, the combination of α and β amino acids comprises β-alanine and at least one α-amino acid selected from the group consisting of glycine, alanine, valine, leucine, iso-leucine, phenylalanine, proline, aspartic acid, glutamic acid, lysine, arginine, histidine, serine, threonine, cysteine, asparagine, and glutamine. In an embodiment, the amino acid is selected from the group consisting of: a) a balanced amino acid having a relatively equal balance between hydrophobic and hydrophilic components or a relatively more hydrophilic amino acid, or b) a combination of (i) a balanced amino acid or a relatively more hydrophilic amino acid and (ii) a hydrophobic amino acid. In an embodiment, the balanced amino acid comprises glycine. In an embodiment, the internal portion comprises glycine and a hydrophobic amino acid selected from iso-leucine, valine, and phenylalanine. In an embodiment, the plurality of granules are blended with a hydrophobic coating material. In an embodiment, the hydrophobic coating material is magnesium stearate. In an embodiment, the hydrophobic coating material is 1% to 3% of the total dosage form weight.

An internal portion as described above can be prepared by a process as disclosed in U.S. Pat. No. 6,517,868, which is incorporated herein by reference for the teachings disclosed therein.

First and Second Coatings

The first coating and the second coating of an extended release bimodal solid dosage form of the present disclosure are non-functional coatings that act as processing aids. The first coating and the second coating do not substantially affect the release of the API from the dosage form. In an embodiment, the first and the second coating comprise a hydrophilic material. In an embodiment, the hydrophilic material is hypromellose. In an embodiment, the hypromellose is Methocel E5. In an embodiment, the first and the second coating further comprise the coating additive plasACRYL™, an aqueous emulsion of glyceryl monostearate and triethyl citrate (developed by Emerson Resources, Inc. of Norristown, Pa., USA). In an embodiment, the plasACRYL™ used in the first and second coatings is T20 grade. In an embodiment, the PlasACRYL™ T20 is a 20% aqueous suspension, containing an anti-tacking agent, a plasticizer and a stabilizer. Hypromellose is a pH independent non-ionic polymer formed by partial substitution with O-methylated and O-(2-hydroxypropylated) groups. The grades of hypromellose can vary upon extent to substitution which affects the viscosity. HPMC K4M Premium exhibits a viscosity of 3550 mPas, while HPMC E5 premium LV is a low viscosity grade polymer having a viscosity of 5 mPas. Hypromellose is soluble in cold water and forms a colloidal viscous liquid.

Drug Layer Overcoat

The drug layer overcoat of an extended release solid dosage form of the present disclosure is an immediate release ("IR") drug layer. In an embodiment, the drug layer overcoat is sufficiently designed to yield a burst of about 25% API, which, when the solid dosage form is ingested orally, would result in about 25% API being released in the stomach. In an embodiment, the drug layer overcoat, or immediate release drug layer, comprises ondansetron hydrochloride, hypromellose and plasACRYL™. In an embodiment, the hypromellose used in the IR layer is Methocel E5.

Additional Layers—Enteric Coating

In an embodiment, an extended release solid dosage form of the present disclosure further includes an enteric coating. In an embodiment, an enteric coating layer is positioned between the first coating and the drug layer overcoat. In an embodiment, the enteric coating layer is EUDRAGIT® L30D-55. In an embodiment, the enteric coating layer is EUDRAGIT® FS 30 D. In an embodiment, the enteric coating layer is SURETERIC®.

The following examples are put forth so as to provide those of ordinary skill in the art with a complete disclosure and description of how to make and use the described invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

EXAMPLES

Example 1

Manufacture of 18 mg Ondansetron Internal Cores

TABLE 1

Ondansetron Internal Core, 18 mg; Amino Acid core ("AA core")

| Item | Ingredients | % w/w | mg/tablet | Actual g/batch |
|---|---|---|---|---|
| 1 | Ondansetron HCl | 3.83 | 20.2† | 298.7* |
| 2 | Glycine, USP | 18.96 | 100 | 1327.01 |
| 3 | Hypromelose, USP (Methocel K15M Premium CR) | 18.96 | 100 | 1327.01 |
| 4 | Microcrystalline Cellulose, NF (Avicel ® PH-102) | 19.84 | 104.7 | 1358.2* |
| 5 | Hypromelose, USP (Methocel K100 Premium LV) | 37.91 | 200 | 2654.03 |
| 6 | Purified Water, USP | | | 1750.0 |
| 7 | Magnesium Stearate, NF | 0.50 | 2.6 | 35.0 |
| | Totals | 100.00 | 527.5 | 7000.00 |

*adjusted based on API potency: MCC reduced to compensate
†20.2 mg of Ondansetron HCl is equivalent to 18 mg of Ondansetron The amino acid formulation ("AA core") was manufactured using low shear wet granulation. The Avicel® PH-102 microcrystalline cellulose, ondansetron HCl, glycine and HPMC K15M were mixed in a 1 cu ft V-blender for 10 minutes, discharged and delumped using a Comil equipped with a 20 mesh screen. The pre-blend was then granulated in the Hobart D300 by adding water to the blend while mixing. After the water was added the material was mixed for an additional 2 minutes. The material was granulated adequately but not overly wet, therefore no additional water was added. The wet mass was screened through an 8 mesh screen then oven dried. The dried granulation was milled using a Comil with an 18 mesh screen, blended with the extragranular HPMC K100LV and lubricant. Compression of the final blend was conducted on a 36-station Kikusui press using the 0.32"×0.58" modified oval tooling.

TABLE 2

Ondansetron Internal Portion, 18 mg; Electrolyte core ("Electrolyte core")

| Item | Ingredients | % w/w | mg/tablet | g/batch |
|---|---|---|---|---|
| 1 | Ondansetron HCl | 5.39 | 20.20† | 601.10* |
| 2 | Hypromelose, USP (Methocel K4M Premium CR) | 26.70 | 100.00 | 2670.23 |
| 3 | Sodium Citrate Anhydrous, USP (fine granular) | 13.35 | 50.00 | 1335.11 |
| 4 | Microcrystalline Cellulose, NF (Avicel ® PH-102) | 54.02 | 202.30 | 5340.2* |
| 5 | Magnesium Stearate, NF (vegetable grade) | 0.53 | 2.00 | 53.40 |
| | Totals | 100.00 | 374.50 | 10000.00 |

*adjusted based on API potency: MCC reduced to compensate
†20.2 mg of Ondansetron HCl is equivalent to 18 mg of Ondansetron The electrolyte formulation ("Electrolyte core") was manufactured by blending and compression. All the materials were screened separately through a 30 mesh hand screen, charged into the V-blender and mixed for 15 minutes then lubricated. Compression was conducted on a 36-station Kikusui press using the 0.28"×0.50" modified oval tooling.

Example 2

First and Second Seal Coatings; Optional Enteric Coating

TABLE 3

Seal Coat Formula (sub coating and top coat)

| Item | Ingredients | % w/w | g/batch* |
|---|---|---|---|
| 1 | Hypromellose (Methocel E5) | 6.00 | 109.2 |
| 2 | PlasACRYL ™T20 | 0.60 | 10.92 |
| 3 | Purified Water | 93.40 | 1699.88 |
| | Total | 100.0 | 1820.00 |

*batch size is for one seal coating, with ~30% overage

TABLE 4

Enteric Coating Formula

| item | Ingredients | % w/w | g/batch* |
|---|---|---|---|
| 1 | EUDRAGIT ® L30D-55 (30% dispersion) | 71.22 | 1365.68 |
| 2 | PlasACRYL ™ T20 (20% emulsion) | 10.68 | 204.13 |
| 3 | Triethyl citrate | 1.08 | 21.24 |
| 4 | Purified Water | 17.02 | 768.86 |
| | Total | 100.00 | 2359.91 |

*batch size includes 30% overage

The seal coating solution was manufactured by dissolving the Methocel E5 in water, then adding the PlasACRYL™. The enteric coating suspension was manufactured by mixing the water, triethyl citrate and PlasACRYL™. The EUDRAGIT® dispersion was added; the suspension was mixed for 30 minutes then screened through a 60 mesh screen. The active suspension was manufactured by first dissolving the Methocel E5 in water, and separately dispersing the ondansetron in water and homogenizing. The Methocel solution was then added to the drug suspension, and the PlasACRYL™ was added.

Example 3

Drug Layer Overcoat

TABLE 5

Drug layer coating Formulas

| | Ingredients | % w/w | 1 g/batch* | 2 g/batch* | 3 g/batch* |
|---|---|---|---|---|---|
| 1 | Ondensatron HCl | 2.40 | 65.82 | 87.76 | 83.37 |
| 2 | Hypromellose (Methocel E5) USP | 3.60 | 98.72 | 131.63 | 0.13 |
| 3 | PlasACRYL ™ (20% emulsion) | 0.90 | 24.68 | 32.91 | 31.26 |
| 4 | Purified Water | 93.10 | 2553.13 | 3404.18 | 3233.97 |
| | Total | 100.00 | 2742.35 | 3656.47 | 3473.65 |

*Batch sizes include an 18% overage to account for manufacturing losses

The tablets were coated with the required coatings as listed in Tables 6-8. Weight gain was monitored by measuring the weight of 50 tablets every 10 minutes. Due to equipment availability, the 1st two batches were coated using the R&D tablet coater (O'Hara LabMX). The 3rd batch was manufactured using the cGMP equipment which will be used for the CTM manufactures.

TABLE 6

Coating Parameters; Product 1
AA core

| O'Hara LabMX | Initial seal coat | IR coat | Final topcoat |
|---|---|---|---|
| Starting charge (kg) | 3.956 | 3.953 | 4.058 |
| Inlet temp (° C.) | 61.8-62.4 | 59.9-62.5 | 61.0-63.1 |
| Outlet temp (° C.) | 42.5-44.1 | 43.5-44.1 | 42.5-45.5 |
| Pan speed (rpm) | 12 | 12 | 12 |
| Spray rate (g/min) | 25.3-27.0 | 24.2-26.5 | 22.1-27.5 |
| Atomization pressure (psi) | 25 | 25 | 25 |
| Inlet airflow (cfm) | 200 | 200 | 200 |
| Final weight gain | 2.05% | 20.9 mg/tablet | 2.09% |
| Coating efficiency | | 100% | |

TABLE 7

Coating Parameters; Product 2
Electrolyte core

| O'Hara LabMX | Initial seal coat | IR coat | Final topcoat |
|---|---|---|---|
| Starting charge | 3.745 | 3.814 | 3.990 |
| Inlet temp (° C.) | 60.5-62.2 | 60.0-61.4 | 61.0-62.8 |
| Outlet temp (° C.) | 42.4-43.8 | 42.2-43.7 | 42.2-44.0 |
| Pan speed (rpm) | 12 | 12 | 12 |
| Spray rate (g/min) | 25.1-26.8 | 25.8-27.6 | 24.2-30.5 |
| Atomization pressure (psi) | 25 | 25 | 25 |
| Inlet airflow (cfm) | 200 | 200 | 200 |
| Final weight gain | 2.12% (79.4 g) | 20.2 mg/tablet | 2.23% |
| Coating efficiency | | 93% | |

TABLE 8

Coating Parameters; Product 3
Electrolyte core, Enteric coat + Drug overcoat

| Driam Driacoater | Initial seal coat | Enteric coat | Drug overcoat | Final topcoat |
|---|---|---|---|---|
| Starting charge | 3.558 | 3.627 | 3.991 | 4.143 |
| Inlet temp (° C.) | 44.0-60.0 | 42-47 | 45-47 | 44-48 |
| Outlet temp (° C.) | 43-48 | 41-46 | 42-44 | 41-45 |
| Pan speed (rpm) | 12 | 12 | 12 | 12 |
| Spray rate (g/min) | 22.7-24.6 | 16.7-19.6 | 23.1-27.3 | 24.7-27.5 |
| Atomization pressure (psi) | 35 | 30-35 | 30 | 30 |
| Inlet airflow (cfm) | 300 | 300 | 300 | 300 |
| Final weight gain | 2.50% | 10.24% | 19.5 mg/tablet | 2.33% |
| Coating efficiency | | | 84.5% | |

TABLE 9

Overall Batches

| | Product # | | | | | | | | |
|---|---|---|---|---|---|---|---|---|---|
| | 1 | | | 2 | | | 3 | | |
| Ingredient | % w/w | Mg/tablet | g/batch | % w/w | Mg/tablet | g/batch | % w/w | Mg/tablet | g/batch |
| Ondansetron CDT tablet, 18 mg | 92.81 | 527.50 | 3956.25 | | | | | | |
| Ondansetron CDT tablet, 18 mg | | | | 91.53 | 374.50 | 3745.00 | 83.57 | 374.50 | 3557.75 |
| Hypromellose seal coat | 1.86 | 10.55 | 79.13 | 1.83 | 7.49 | 74.90 | 1.67 | 7.49 | 71.16 |
| Enteric coating (Eudragit ®) | | | | | | | 8.52 | 38.20 | 362.90 |
| Ondansetron drug overcoat | 3.37 | 19.15* | 143.63 | 4.68 | 19.15* | 191.50 | 4.27 | 19.15* | 181.93 |
| Hypromellose seal coat | 1.96 | 11.14 | 83.58 | 1.96 | 8.02 | 80.23 | 1.96 | 8.79 | 83.47 |
| Total | 100.00 | 568.34 | 4262.58 | 100.00 | 409.16 | 4091.63 | 100.00 | 448.13 | 4257.20 |

Example 4

Dissolution Profile

TABLE 10

| | | Dissolution (Ondansetron Bimodal Release Tablets, 24 mg) | | | | | | |
|---|---|---|---|---|---|---|---|---|
| | | Product 1 Amino acid | | Product 2 Electrolyte | | | Product 3 Electrolyte | |
| Tablet strength (mg) | | 24 | | 24 | | | 24 | |
| Apparatus | | II (paddle) | | II (paddle) | | | II (paddle) | |
| Sinker | | Japanese basket | | Japanese basket | | | Japanese basket | |
| # units | | 6 | | 6 | | | 6 | |
| Speed (rpm) | | 50 | | 50 | | | 50 | |
| Dissolution media | Time point (hrs) | Mean % dissolved | % RSD | Mean % dissolved | % RSD | | Mean % dissolved | % RSD |
| water | 0.5 | 25.8 | 9.9 | 25.3 | 6.7 | 0.1N HCl | 25.2 | 4.8 |
| | 2 | 38 | 5.5 | 41.4 | 4 | | 25.8 | 4.9 |
| | 3 | 45.1 | 5.4 | 51.1 | 3.4 | pH 6.8 | 33.8 | 7.8 |
| | 4 | 50.6 | 4.9 | 58.1 | 3.4 | phosphate | 44 | 4.9 |
| | 6 | 60 | 4.1 | 69.7 | 3.8 | buffer | 61.4 | 5.4 |
| | 9 | 71.5 | 3.9 | 82.7 | 4.2 | | 79.7 | 2.7 |
| | 12 | 79.5 | 3.6 | 93.1 | 4.1 | | 89.5 | 2.5 |
| | 15 | 84.6 | 3.4 | 99.2 | 4.1 | | 95.8 | 3.6 |
| | 18 | 88 | 3.4 | 102.5 | 3.8 | | 98.6 | 3.1 |
| | 21 | 90.8 | 3.3 | 103.8 | 3.7 | | 100 | 3.6 |
| | 24 | 93.1 | 3.1 | 104.6 | 3.6 | | 101.6 | 3.4 |

Figure 2:
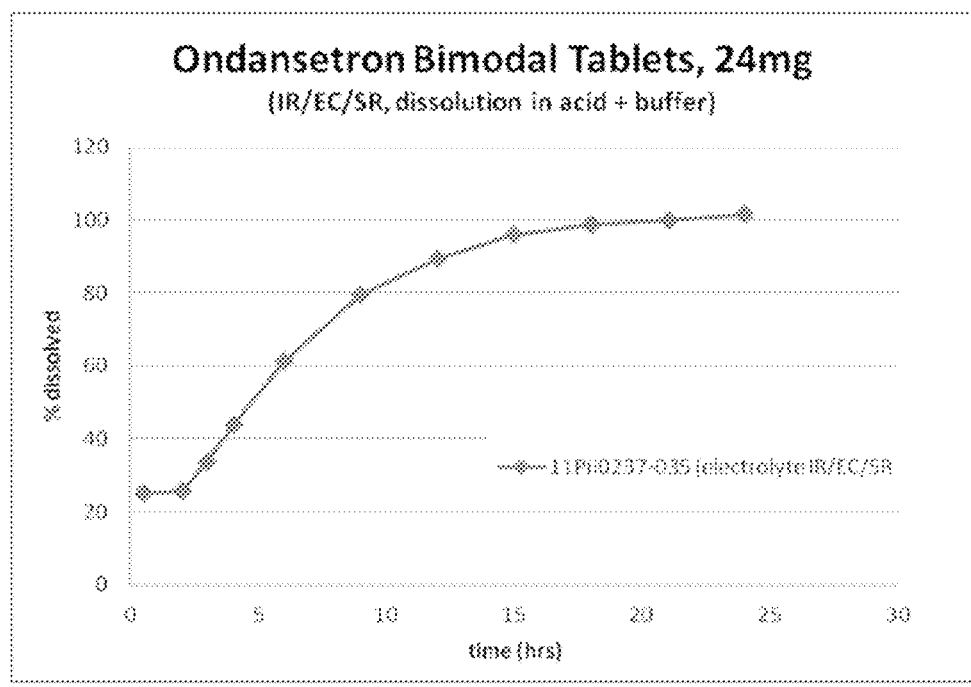
FIG. 2 illustrates the dissolution profile of ondansetron from an embodiment of an extended release solid dosage form of the present disclosure as measured using a USP type 2 (paddle) dissolution system at 50 rpm, at a temperature of 37±0.5° with 0.1N HCL and pH 6.8 phosphate buffer as a dissolution medium.

Table 10 in conjunction with FIG. 1 and FIG. 2 show the dissolution profile for Products 1, 2 and 3. For product 1, there was an initial 25% burst, followed by a sustained release over 24 hours. For product 2, there was an initial 25% burst, followed by a sustained release over 24 hours. For product 3, there was initial 25% burst, followed by a lag in release while in acid.

Example 5

Manufacture of Ondansetron Internal Electrolyte Core

Figure 3:
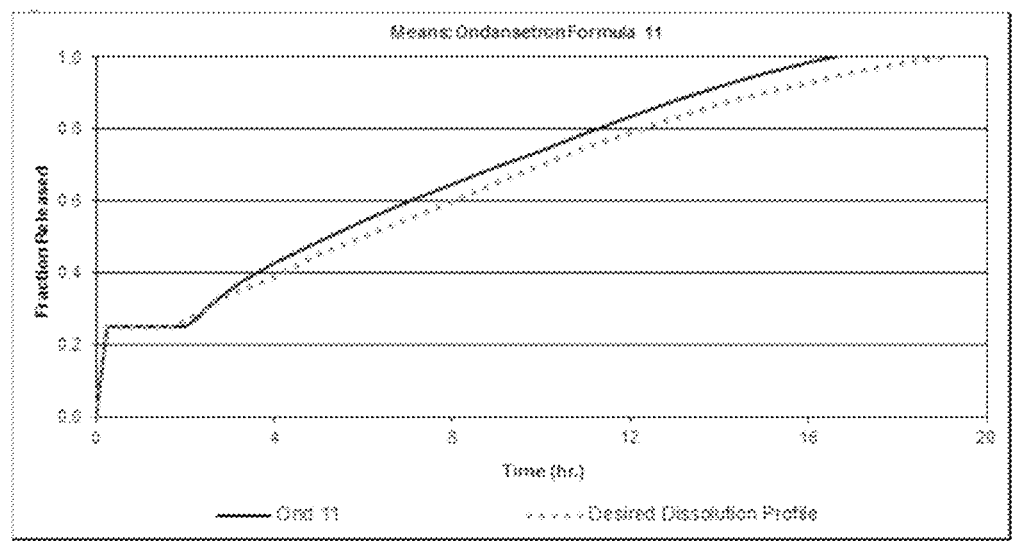
FIG. 3 illustrates the dissolution profile of ondansetron from an embodiment of an extended release solid dosage form of the present disclosure as measured using a USP type 2 (paddle) dissolution system at 50 rpm, at a temperature of 37±0.5° with 0.1N HCL and pH 6.8 phosphate buffer as a dissolution medium.

Ondansetron HCl tablet cores were prepared through dry-blend and direct compression. Details of the formulation ingredients are depicted in Tables 11 and 12. The dissolution profile (assuming enteric coating and 6 mg immediate release drug coating) for this formula is shown in FIG. 3.

TABLE 11

| Ondansetron Electrolyte 11- tablet core | | |
|---|---|---|
| Ondansetron HCl Electrolyte 11 | % w/w | mg/dosage |
| Ondansetron HCl | 5.30% | 22.5 |
| sodium citrate | 11.78% | 50 |
| HPMC K4M | 23.56% | 100 |
| MCC | 47.11% | 200 |
| mg stearate | 0.47% | 2 |
| Total | | 374.5 |

TABLE 12

| 22.5 mg Ondansetron HCl Formulation 11 | | | | | |
|---|---|---|---|---|---|
| Raw Material | Purpose | Manufacturer | Lot Number | w/w % | mg/dosage |
| Ondansetron HCl | API | DRL | ON01 31 05 | 5.30% | 22.5 |
| HPMC K4M | Polymer | Colorcon | WP193724 | 23.56% | 100.00 |
| Sodium Citrate | Electrolyte | Gadot Biochemical Ind. | 48010004 | 11.78% | 50.00 |
| Avicel MCC PH 102 | Flow Agent | FMC Biopolymer | P208819629 | 47.11% | 200.00 |
| Mg Stearate | Lubricant | Mallinckrodt | E17591 | 0.47% | 2.00 |
| Total | | | | 100% | 374.5 |

Example 6

Dissolution Profile

Figure 4:
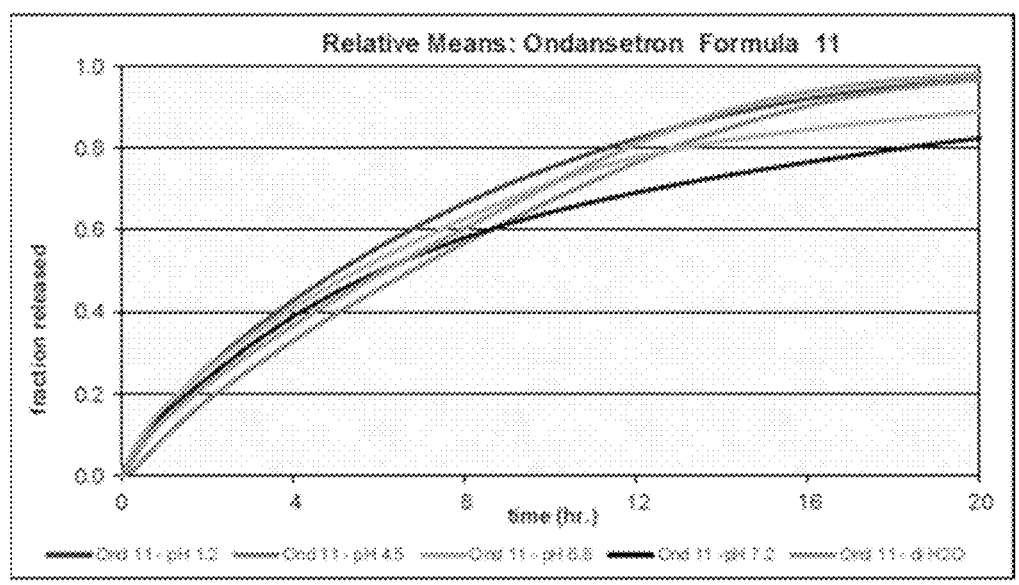
FIG. 4 illustrates the dissolution profiles of ondansetron from an embodiment of an extended release solid dosage form of the present disclosure as measured using a USP type 2 (paddle) dissolution system at 50 rpm, at a temperature of 37±0.5° with physiologically relevant media within a pH range of 1.2 to 7.2, approximating levels found through the GI tract.

In vitro dissolution was performed with physiologically relevant media within a pH range of 1.2 to 7.2, approximating levels found through the GI tract. Due to differences in solubility at various pH of the ondansetron HCl API, absorbance max was used to calculate dissolution release rather than the calibration curve created with the API in water. Dissolution testing results for media: pH1.2, 4.5, 6.8, 7.2 and diH$_2$O can be seen in FIG. 4.

Example 7

In Vivo Testing of Solid Dosage Forms

A single center, randomized, laboratory-blinded, 4-period, 4-sequence, crossover design study was carried out in healthy male and female subjects. The following investigational products were to be administered under fasting conditions:

Test-1: 1× Ondansetron 24 mg bimodal tablet (amino acid core) Batch no.: 19401.001A Test-2: 1× Ondansetron 24 mg bimodal tablet (electrolyte core) Batch no.: 19404.001A Test-3: 1× Ondansetron 24 mg bimodal tablet (enteric coated electrolyte core) Batch no.: 19403.001A Reference: 3× Zofran® 8 mg tablets (1×8 mg tablet administered three-times daily, at 8-hour intervals: in the morning following a 10-hour overnight fast, in the afternoon and in the evening)

The products were to be administered to 28 healthy male and female subjects according to Table 13.

|  | Period 1 | Period 2 | Period 3 | Period 4 |
|---|---|---|---|---|
| Sequence 1 (n = 7) | Test-1 | Reference | Test-2 | Test-3 |
| Sequence 2 (n = 7) | Test-2 | Test-1 | Test-3 | Reference |
| Sequence 3 (n = 7) | Test-3 | Test-2 | Reference | Test-1 |
| Sequence 4 (n = 7) | Reference | Test-3 | Test-1 | Test-2 |

Selection of Doses in the Study

The dose was chosen to achieve similar exposure as with the marketed immediate-release formulation (Zofran® 8 mg) when administered three-time daily.

Selection and Timing of Dose for Each Subject

Subjects fasted overnight for at least 10 hours prior to morning drug administration.

Tests 1-3

A single dose of the assigned Test formulation was administered orally with approximately 240 mL of water at ambient temperature, starting at 07:30, to one subject per minute.

Reference

The assigned Reference formulation was administered orally (three-times daily, at 8-hour intervals) with approximately 240 mL of water at ambient temperature, starting at 07:30, to one subject per minute. Subsequent drug administrations took place in the afternoon and in the evening at 15:30 and 23:30, respectively.

Fasting continued for at least 4 hours following morning drug administration, after which a standardized lunch was served. The lunch was to be completed no later than 5 hours following morning drug administration. All meals were served at appropriate times thereafter, but not before 9 hours after morning drug administration. The supper was not to be served before 11 hours after the morning drug administration and was to be completed no later than 13 hours following morning drug administration. Furthermore, the light snack was to be completed no later than 13 hours after the morning drug administration. Water was allowed ad libitum until 1 hour pre-dose and beginning 1 hour after each drug administration.

Efficacy and Safety Measurements Assessed and Flow Chart Pharmacokinetic Assessments Blood samples for pharmacokinetic measurements were collected prior to and up to 32 hours (serial sampling) after each morning drug administration. The direct measurements of this study were the plasma concentrations of ondansetron. These concentrations were obtained by analysis of the plasma derived from the blood samples drawn during this study. The total volume of blood collected per subject (639 mL for males and 653 mL for females) is considered to have a negligible or no impact on the pharmacokinetic profiles of the drugs and the assessment of bioequivalence. Furthermore, it is considered to have a negligible impact on subjects' safety.

Drug Concentration Measurements

Tests 1-3 (21 Blood Samples):

The first blood sample of each period, i.e. the blank plasma sample, was collected prior to drug administration while the others were collected 0.25, 0.5, 1, 1.5, 2, 2.5, 3, 3.5, 4, 5, 6, 7, 8, 9, 10, 12, 16, 20, 24 and 32 hours after drug administration in one tube of 6 mL (K$_2$ EDTA Vacutainers)

Reference (33 Blood Samples):

The first blood sample of each period, i.e. the blank plasma sample, was collected prior to the morning drug administration while the others were collected 0.25, 0.5, 1, 1.5, 2, 2.5, 3, 4, 6, 8, 8.25, 8.5, 9, 9.5, 10, 10.5, 11, 12, 14, 16, 16.25, 16.5, 17, 17.5, 18, 18.5, 19, 20, 22, 24, 28 and 32 hours following the morning drug administration in one tube of 6 mL (K2 EDTA Vacutainers). Samples at 8-hour and 16-hour were collected within 5 minutes before the drug administration (the afternoon and evening administrations).

Ondansetron—Test-1 vs Reference

Figure 5:
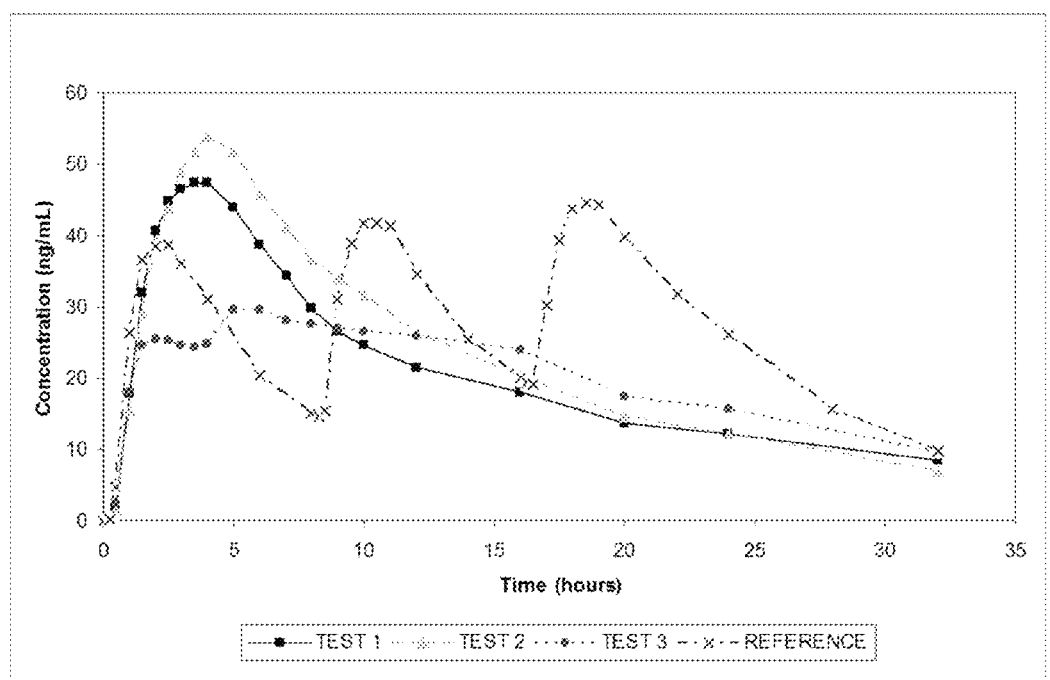
FIG. 5 illustrates the mean measured plasma concentration versus time profile of ondansetron, derived from the administration of various embodiments of extended release solid dosage forms of the present disclosure and a reference product.
Figure 6:
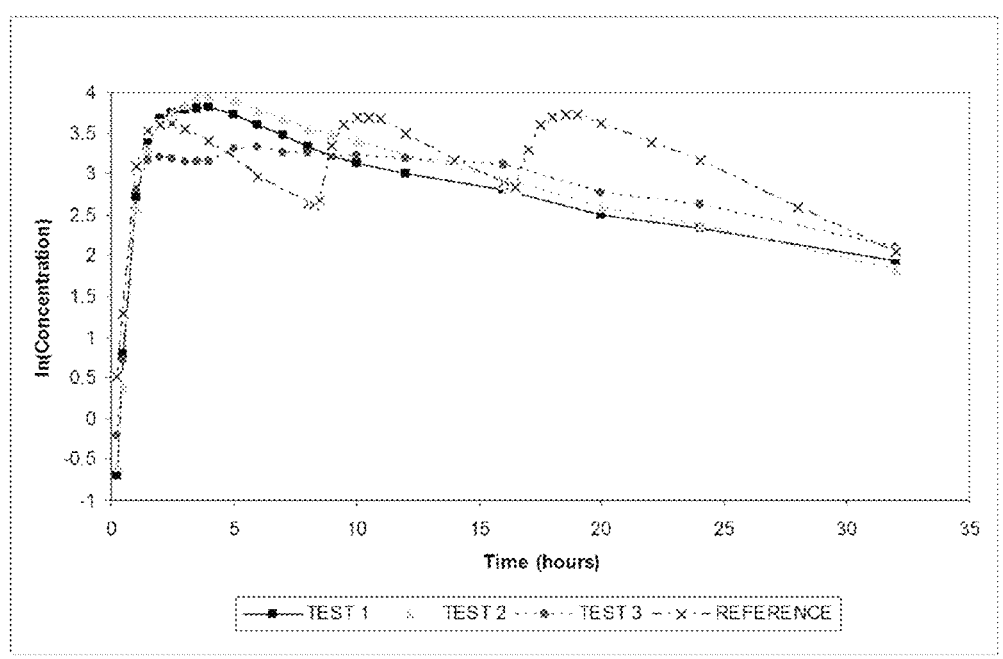
FIG. 6 illustrates the ln-transformed mean concentration versus time profile of ondansetron, derived from the administration of various embodiments of extended release solid dosage forms of the present disclosure and a reference product.
Figure 7:
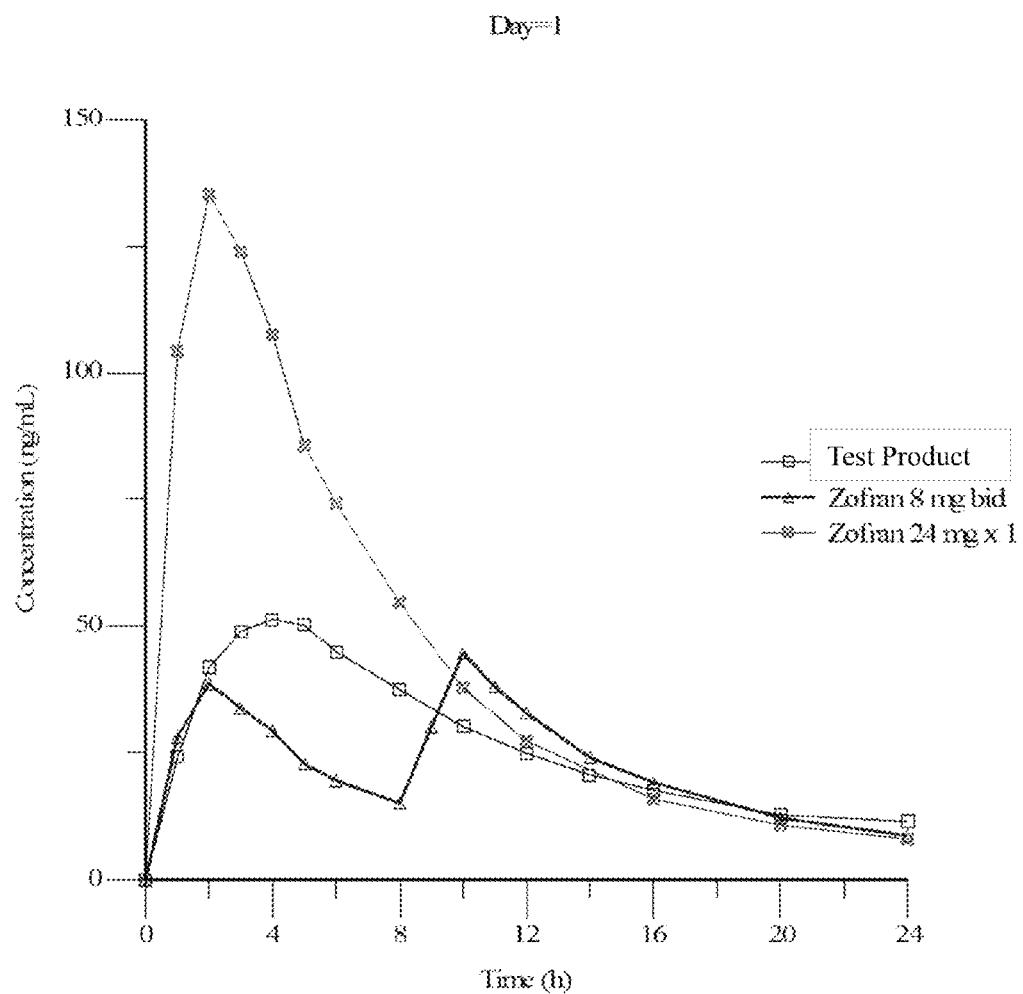
FIG. 7 illustrates the linear mean measured plasma concentration versus time profile of Test Product at day 1, derived from the administration of an embodiment of an extended release solid dosage form of the present disclosure and a reference product.
Figure 8:
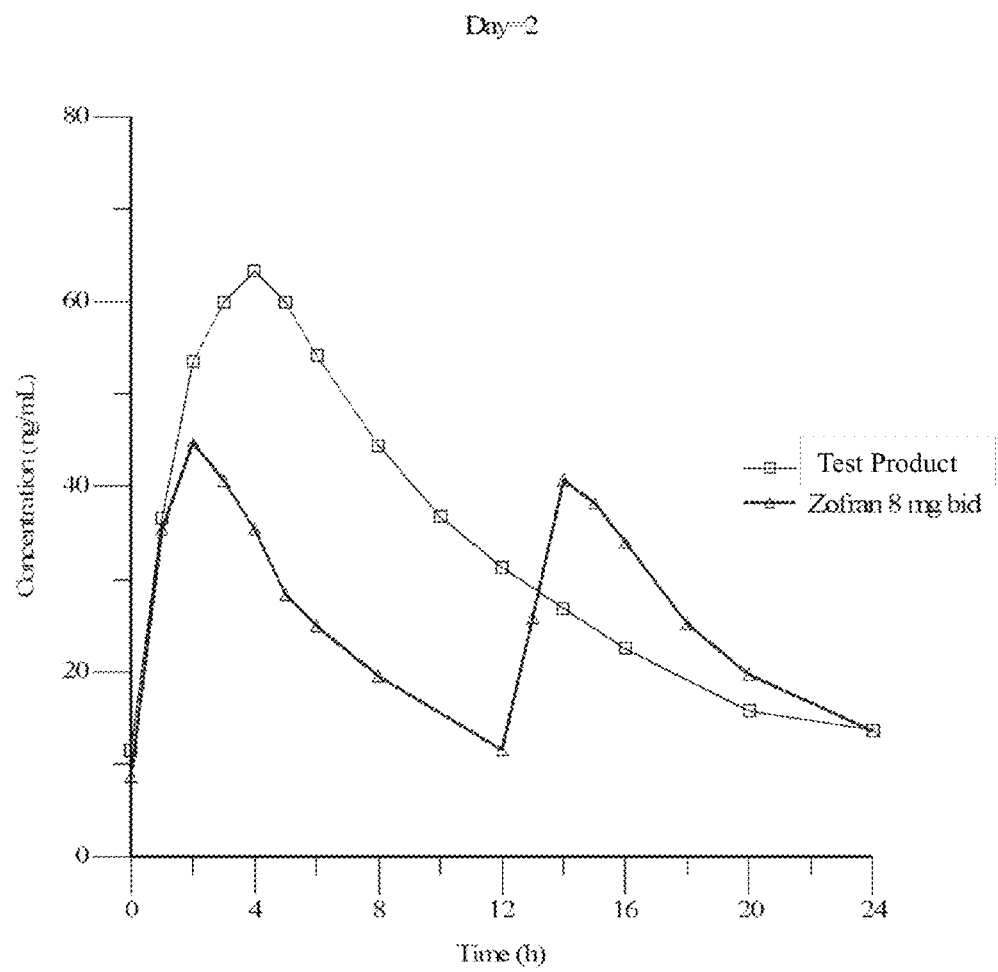
FIG. 8 illustrates the linear mean measured plasma concentration versus time profile of Test Product at day 2, derived from the administration of an embodiment of an extended release solid dosage form of the present disclosure and a reference product.
Figure 9:
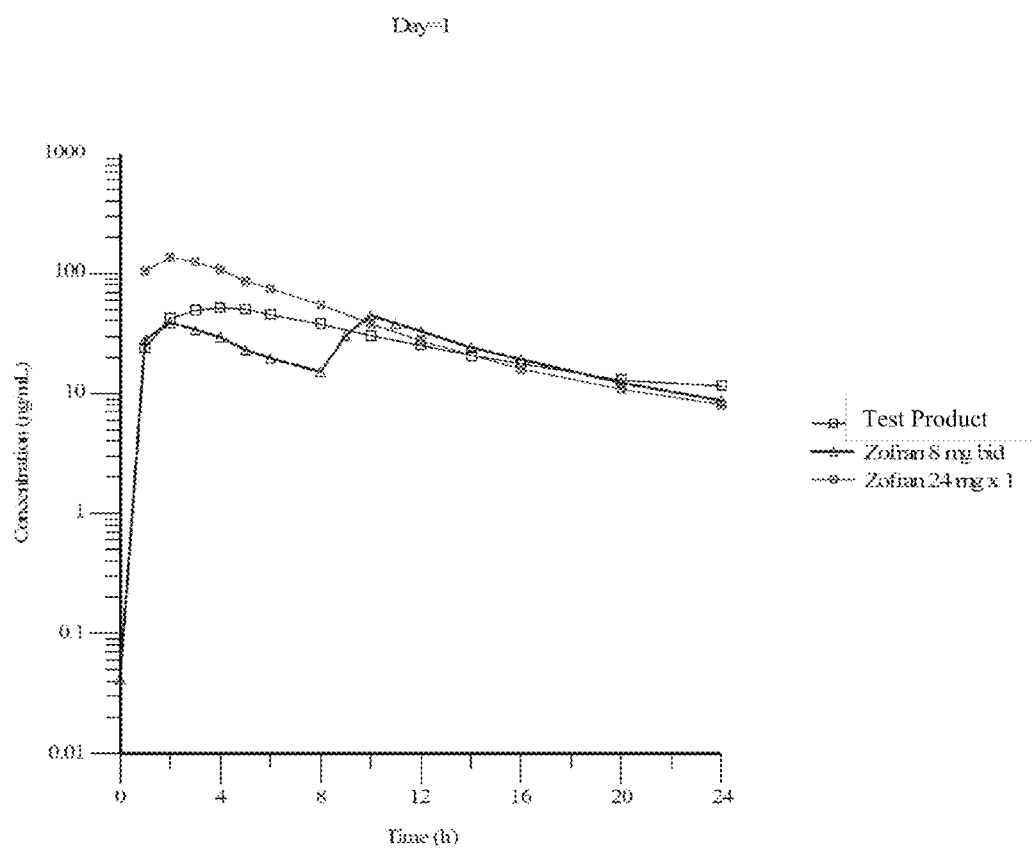
FIG. 9 illustrates the ln-transformed mean concentration versus time profile of Test Product at day 1, derived from the administration of an embodiment of an extended release solid dosage form of the present disclosure and a reference product.
Figure 10:
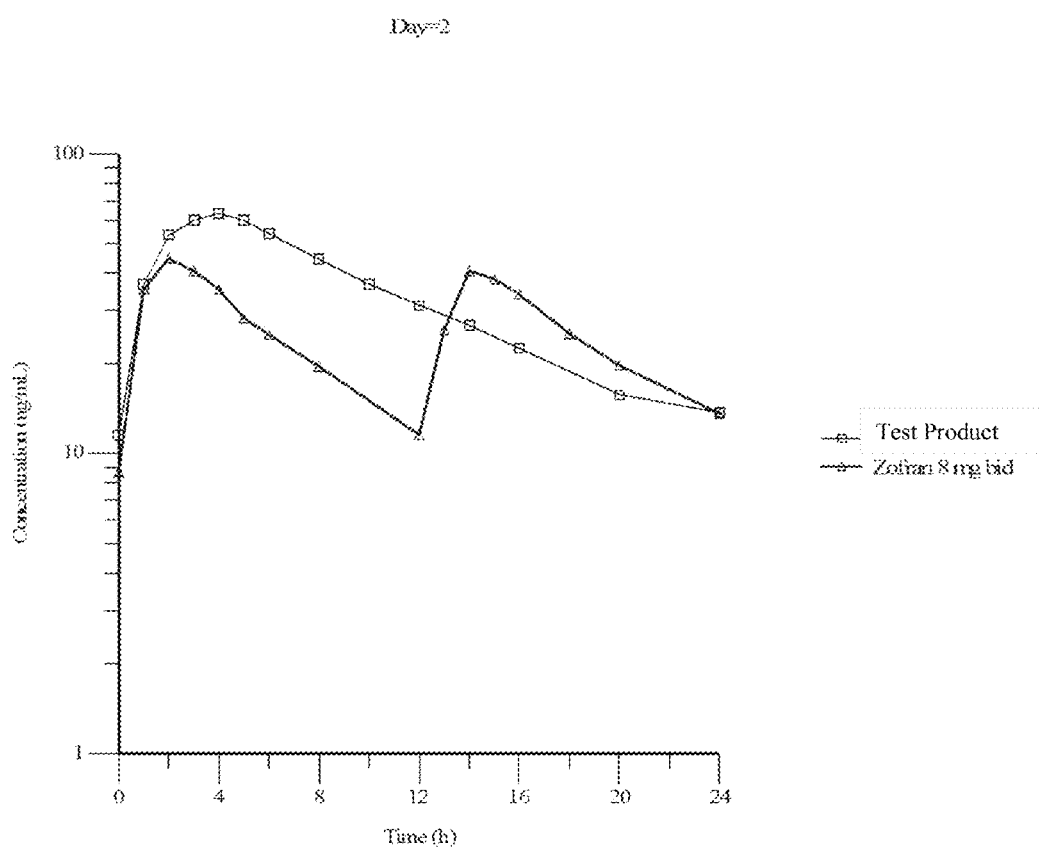
FIG. 10 illustrates the ln-transformed mean concentration versus time profile of Test Product at day 2, derived from the administration of an embodiment of an extended release solid dosage form of the present disclosure and a reference product.
Figure 11:
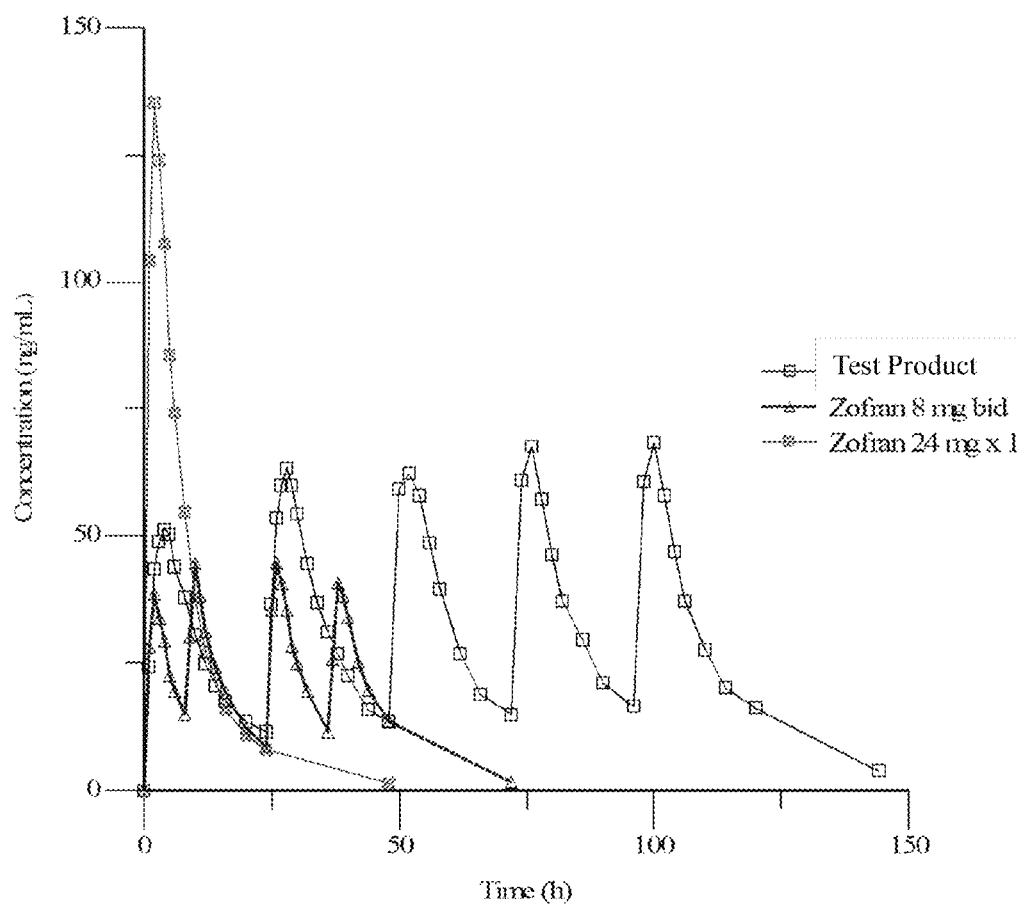
FIG. 11 illustrates the linear overall profile of the mean measured plasma concentration versus time profile of Test Product and reference product, derived from the administration of an embodiment of an extended release solid dosage form of the present disclosure and the reference product.
Figure 12:
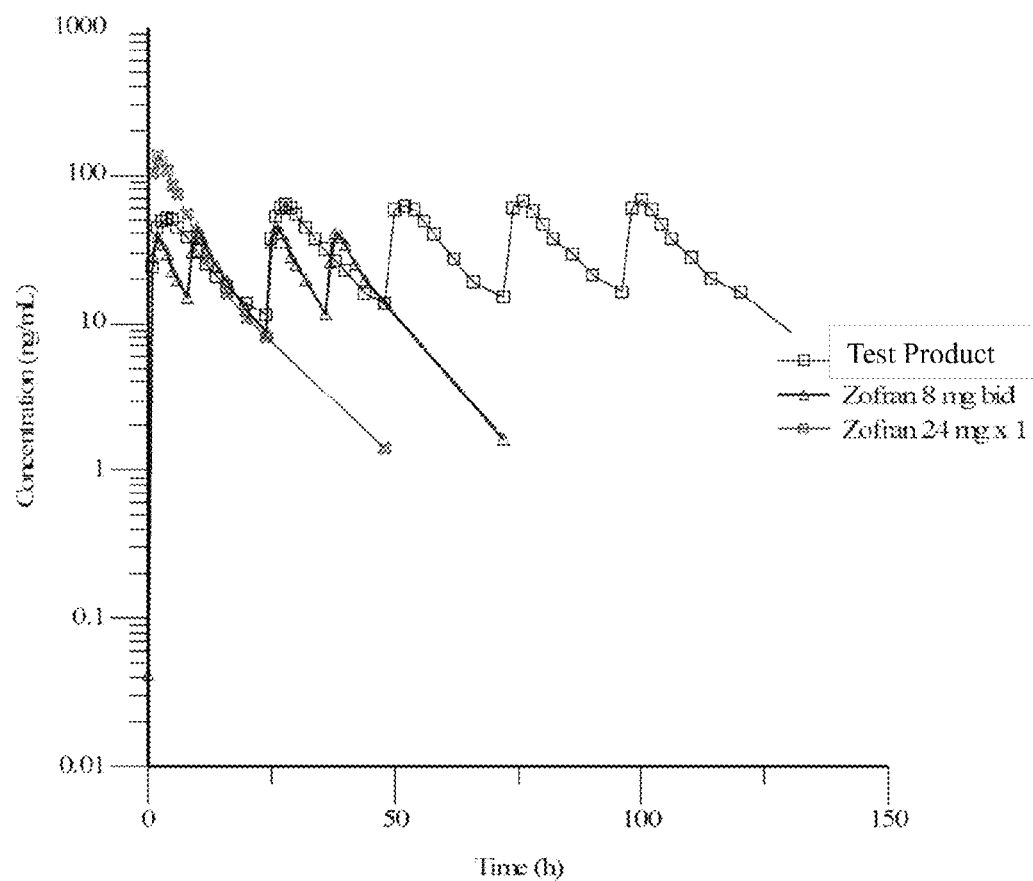
FIG. 12 illustrates the ln-transformed overall profile of the mean measured plasma concentration versus time profile of Test Product and reference product, derived from the administration of an embodiment of an extended release solid dosage form of the present disclosure and the reference product.

Twenty-six (26) subjects were included in the comparison between Test-1 and Reference. A summary of the pharmacokinetic parameters and the standards for comparative bioavailability are presented in Tables 14 and 15. The mean measured plasma concentration versus time profile, derived from the administration of the Test-1 and Reference products, is depicted in FIG. 5, whereas the ln-transformed mean concentration versus time profile is depicted in FIG. 6.

TABLE 14

Summary of Main Study Results - Ondansetron - Test-1 vs Reference

| PARAMETER | TEST-1 | | REFERENCE | |
|---|---|---|---|---|
|  | MEAN | C.V. (%) | MEAN | C.V. (%) |
| $C_{max}$ (ng/mL) | 50.669 | 30.3 | 50.731 | 30.5 |
| ln ($C_{max}$) | 3.8742 | 8.8 | 3.8835 | 7.7 |
| $T_{max}$ (hours) § | 3.50 | 23.6 | 17.50 | 45.7 |
| $AUC_T$ (ng · h/mL) | 659.098 | 34.5 | 854.517 | 37.4 |
| ln ($AUC_T$) | 6.4337 | 5.4 | 6.6897 | 5.3 |
| $AUC_\infty$ (ng · h/mL) | 795.397 | 43.3 | 946.030 | 43.5 |
| ln ($AUC_\infty$) | 6.5921 | 6.5 | 6.7741 | 5.8 |
| $AUC_{T/\infty}$ (%) | 84.61 | 12.2 | 92.07 | 5.8 |

TABLE 14-continued

Summary of Main Study Results -
Ondansetron - Test-1 vs Reference

|  | TEST-1 | | REFERENCE | |
|---|---|---|---|---|
| PARAMETER | MEAN | C.V. (%) | MEAN | C.V. (%) |
| $K_{el}$ (hours$^{-1}$) | 0.0671 | 29.8 | 0.1391 | 26.7 |
| $T_{1/2el}$ (hours) | 11.72 | 46.3 | 5.40 | 31.5 |
| $AUC_{0-24}$ (ng · h/mL) | 577.151 | 32.6 | 720.455 | 33.6 |
| $C_{24}$ (ng/mL) | 12.134 | 58.3 | 26.115 | 50.6 |

§ For $T_{max}$, the median is presented

TABLE 15

Comparison of Results with Standards for Bioequivalence -
Ondansetron - Test-1 vs Reference

| PARAMETER | INTRA-SUBJECT C.V. (%) | GEOMETRIC LSMEANS* | | RATIO (%) | 90% CONFIDENCE LIMITS (%) | |
|---|---|---|---|---|---|---|
| | | TEST-1 | REFERENCE | | LOWER | UPPER |
| $C_{max}$ | 14.0 | 48.222 | 48.685 | 99.05 | 92.89 | 105.62 |
| $AUC_T$ | 11.3 | 625.797 | 807.106 | 77.54 | 73.60 | 81.68 |
| $AUC_\infty$ | 14.3 | 738.123 | 879.247 | 83.95 | 78.46 | 89.82 |

*units are ng/mL for $C_{max}$ and ng · h/mL for $AUC_T$ and $AUC_\infty$

The number of subjects included in the statistical analysis of these parameters was n=24 for the Test-1 and n=26 for the Reference. The mean $C_{max}$ were respectively, 50.669 ng/mL and 50.731 ng/mL for the Test-1 and Reference formulations. The Test-1 to Reference $C_{max}$ ratio of geometric LSmeans was 99.05% (90% CI: 92.89 to 105.62%). This result thus demonstrates that the ratio and corresponding 90% confidence interval of the relative $C_{max}$ geometric LSmeans of the Test-1 to Reference formulation are within the pre-specified 80.00 to 125.00% range. The median $T_{max}$ was 3.50 and 17.50 hours for the Test-1 and Reference formulations, respectively. The mean $AUC_T$ were respectively, 659.098 ng·h/mL and 854.517 ng·h/mL for the Test-1 and Reference formulations. The Test-1 to Reference $AUC_T$ ratio of geometric LSmeans was 77.54% (90% CI: 73.60 to 81.68%). This result thus demonstrates that the ratio and corresponding 90% confidence interval of the relative $AUC_T$ geometric LSmeans of the Test-1 to Reference formulation are outside the pre-specified 80.00 to 125.00% range. The mean $K_{el}$ was 0.0671 hours$^{-1}$ for the Test-1 formulation and 0.1391 hours$^{-1}$ for the Reference formulation. The mean $T_{1/2el}$ value was 11.72 and 5.40 hours, for the Test-1 and Reference formulations, respectively. The mean $AUC_\infty$ were respectively, 795.397 ng·h/mL and 946.030 ng·h/mL for the Test-1 and Reference formulations. The Test-1 to Reference $AUC_\infty$ ratio of geometric LSmeans was 83.95% (90% CI: 78.46 to 89.82%). This result thus demonstrates that the 90% confidence interval of the relative $AUC_\infty$ geometric LSmeans of the Test-1 to Reference formulation is outside the pre-specified 80.00 to 125.00% range. The mean $AUC_T$ over $AUC_\infty$ individual ratio ($AUC_{T/\infty}$) were respectively, 84.61% and 92.07% for the Test-1 and Reference formulations.

Ondansetron—Test-2 vs Reference

Twenty-six (26) subjects were included in the comparison between Test-2 and Reference. A summary of the pharmacokinetic parameters and the standards for comparative bioavailability are presented in Tables 16 and 17. The mean measured plasma concentration versus time profile, derived from the administration of the Test-2 and Reference products, is depicted in FIG. 5, whereas the ln-transformed mean concentration versus time profile is depicted in FIG. 6.

TABLE 16

Summary of Main Study Results -
Ondansetron - Test-2 vs Reference

|  | TEST-2 | | REFERENCE | |
|---|---|---|---|---|
| PARAMETER | MEAN | C.V. (%) | MEAN | C.V. (%) |
| $C_{max}$ (ng/mL) | 55.718 | 24.0 | 50.731 | 30.5 |
| ln ($C_{max}$) | 3.9889 | 6.7 | 3.8835 | 7.7 |
| $T_{max}$ (hours) § | 4.00 | 13.6 | 17.50 | 45.7 |
| $AUC_T$ (ng · h/mL) | 730.199 | 31.7 | 854.517 | 37.4 |
| ln ($AUC_T$) | 6.5477 | 4.7 | 6.6897 | 5.3 |
| $AUC_\infty$ (ng · h/mL) | 847.660 | 37.7 | 946.030 | 43.5 |
| ln ($AUC_\infty$) | 6.6836 | 5.2 | 6.7741 | 5.8 |
| $AUC_{T/\infty}$ (%) | 87.44 | 5.9 | 92.07 | 5.8 |
| $K_{el}$ (hours$^{-1}$) | 0.0676 | 23.0 | 0.1391 | 26.7 |
| $T_{1/2el}$ (hours) | 10.84 | 25.8 | 5.40 | 31.5 |
| $AUC_{0-24}$ (ng · h/mL) | 653.663 | 29.5 | 720.455 | 33.6 |
| $C_{24}$ (ng/mL) | 12.088 | 52.4 | 26.115 | 50.6 |

§ For $T_{max}$, the median is presented

TABLE 17

Comparison of Results with Standards for Bioequivalence -
Ondansetron - Test-2 vs Reference

| PARAMETER | INTRA-SUBJECT C.V. (%) | GEOMETRIC LSMEANS* | | RATIO (%) | 90% CONFIDENCE LIMITS (%) | |
|---|---|---|---|---|---|---|
| | | TEST-2 | REFERENCE | | LOWER | UPPER |
| $C_{max}$ | 14.0 | 54.008 | 48.685 | 110.93 | 104.03 | 118.30 |
| $AUC_T$ | 11.3 | 700.467 | 807.106 | 86.79 | 82.38 | 91.43 |
| $AUC_\infty$ | 14.3 | 803.436 | 879.247 | 91.38 | 85.57 | 97.58 |

*units are ng/mL for $C_{max}$ and ng · h/mL for $AUC_T$ and $AUC_\infty$

The mean $C_{max}$ were respectively, 55.718 ng/mL and 50.731 ng/mL for the Test-2 and Reference formulations. The Test-2 to Reference $C_{max}$ ratio of geometric LSmeans was 110.93% (90% CI: 104.03 to 118.30%). This result thus demonstrates that the ratio and corresponding 90% confidence interval of the relative $C_{max}$ geometric LSmeans of the Test-2 to Reference formulation are within the pre-specified 80.00 to 125.00% range. The median $T_{max}$ was 4.00 and 17.50 hours for the Test-2 and Reference formulations, respectively. The mean $AUC_T$ were respectively, 730.199 ng·h/mL and 854.517 ng·h/mL for the Test-2 and Reference formulations. The Test-2 to Reference $AUC_T$ ratio of geometric LSmeans was 86.79% (90% CI: 82.38 to 91.43%). This result thus demonstrates that the ratio and corresponding 90% confidence interval of the relative $AUC_T$ geometric LSmeans of the Test-2 to Reference formulation are within the pre-specified 80.00 to 125.00% range. The mean $K_{el}$ was 0.0676 hours$^{-1}$ for the Test-2 formulation and 0.1391 hours$^{-1}$ for the Reference formulation. The mean $T_{1/2el}$ value was 10.84 and 5.40 hours, for the Test-2 and Reference formulations, respectively. The mean $AUC_\infty$ were respectively, 847.660 ng·h/mL and 946.030 ng·h/mL for the Test-2 and Reference formulations. The Test-2 to Reference $AUC_\infty$ ratio of geometric LSmeans was 91.38% (90% CI: 85.57 to 97.58%). This result thus demonstrates that the ratio and corresponding 90% confidence interval of the relative AUC$_\infty$ geometric LSmeans of the Test-2 to Reference formulation are within the pre-specified 80.00 to 125.00% range. The mean AUC$_T$ over AUC$_\infty$ individual ratio (AUC$_{T/\infty}$) were respectively, 87.44% and 92.07% for the Test and Reference formulations.

Ondansetron—Test-3 vs Reference

Twenty-five (25) observations were included for the Test-3 and 26 observations were included for the Reference. A summary of the pharmacokinetic parameters and the standards for comparative bioavailability are presented in Tables 18 and 19. The mean measured plasma concentration versus time profile, derived from the administration of the Test-3 and Reference products, is depicted in FIG. 5, whereas the ln-transformed mean concentration versus time profile is depicted in FIG. 6.

TABLE 18

Summary of Main Study Results - Ondansetron - Test-3 vs Reference

| PARAMETER | TEST-3 MEAN | C.V. (%) | REFERENCE MEAN | C.V. (%) |
|---|---|---|---|---|
| $C_{max}$ (ng/mL) | 32.958 | 28.6 | 50.731 | 30.5 |
| ln ($C_{max}$) | 3.4514 | 9.1 | 3.8835 | 7.7 |
| $T_{max}$ (hours) § | 5.00 | 52.2 | 17.50 | 45.7 |
| AUC$_T$ (ng · h/mL) | 646.611 | 34.6 | 854.517 | 37.4 |
| ln (AUC$_T$) | 6.4122 | 5.6 | 6.6897 | 5.3 |
| AUC$_\infty$ (ng · h/mL) | 830.321 | 47.2 | 946.030 | 43.5 |
| ln (AUC$_\infty$) | 6.6320 | 6.3 | 6.7741 | 5.8 |
| AUC$_{T/\infty}$ (%) | 80.15 | 13.7 | 92.07 | 5.8 |
| $K_{el}$ (hours$^{-1}$) | 0.0640 | 38.3 | 0.1391 | 26.7 |
| $T_{1/2el}$ (hours) | 12.73 | 44.2 | 5.40 | 31.5 |
| AUC$_{0-24}$ (ng · h/mL) | 546.657 | 32.9 | 720.455 | 33.6 |
| $C_{24}$ (ng/mL) | 15.553 | 50.8 | 26.115 | 50.6 |

§ For $T_{max}$, the median is presented

TABLE 19

Comparison of Results with Standards for Bioequivalence - Ondansetron - Test-3 vs Reference

| PARAMETER | INTRA-SUBJECT C.V. (%) | GEOMETRIC LSMEANS* TEST-3 | GEOMETRIC LSMEANS* REFERENCE | RATIO (%) | 90% CONFIDENCE LIMITS (%) LOWER | 90% CONFIDENCE LIMITS (%) UPPER |
|---|---|---|---|---|---|---|
| $C_{max}$ | 14.0 | 31.973 | 48.685 | 65.67 | 61.54 | 70.09 |
| AUC$_T$ | 11.3 | 617.172 | 807.106 | 76.47 | 72.54 | 80.61 |
| AUC$_\infty$ | 14.3 | 777.120 | 879.247 | 88.38 | 82.53 | 94.65 |

*units are ng/mL for $C_{max}$ and ng · h/mL for AUC$_T$ and AUC$_\infty$

The number of subjects included in the statistical analysis of these parameters was n=23 for the Test-3 and n=26 for the Reference. The mean $C_{max}$ were respectively, 32.958 ng/mL and 50.731 ng/mL for the Test-3 and Reference formulations. The Test-3 to Reference $C_{max}$ ratio of geometric LSmeans was 65.67% (90% CI: 61.54 to 70.09%). This result thus demonstrates that the ratio and corresponding 90% confidence interval of the relative $C_{max}$ geometric LSmeans of the Test-3 to Reference formulation are outside the pre-specified 80.00 to 125.00% range. The median $T_{max}$ was 5.00 and 17.50 hours for the Test-3 and Reference formulations, respectively. The mean AUC$_T$ were respectively, 646.611 ng·h/mL and 854.517 ng·h/mL for the Test-3 and Reference formulations. The Test-3 to Reference AUC$_T$ ratio of geometric LSmeans was 76.47% (90% CI: 72.54 to 80.61%). This result thus demonstrates that the ratio and corresponding 90% confidence interval of the relative AUC$_T$ geometric LSmeans of the Test-3 to Reference formulation are outside the pre-specified 80.00 to 125.00% range. The mean $K_{el}$ was 0.0640 hours$^{-1}$ for the Test-3 formulation and 0.1391 hours$^{-1}$ for the Reference formulation. The mean $T_{1/2el}$ value was 12.73 and 5.40 hours, for the Test-3 and Reference formulations, respectively. The mean AUC$_\infty$ were respectively, 830.321 ng·h/mL and 946.030 ng·h/mL for the Test-3 and Reference formulations. The Test-3 to Reference AUC$_\infty$ ratio of geometric LSmeans was 88.38% (90% CI: 82.53 to 94.65%). This result thus demonstrates that the ratio and corresponding 90% confidence interval of the relative AUC$_\infty$ geometric LSmeans of the Test-3 to Reference formulation are within the pre-specified 80.00 to 125.00% range. The mean AUC$_T$ over AUC$_\infty$ individual ratio (AUC$_{T/\infty}$) were respectively, 80.15% and 92.07% for the Test-3 and Reference formulations.

Example 8

3-Arm Crossover Comparative Bioavailability Study of Solid Dosage Forms 3-arm crossover comparative bioavailability study of five day dosing of solid dosage forms of the present invention once daily versus two day dosing of twice daily ondansetron 8 mg immediate-release tablets versus a single dose of ondansetron 24 mg immediate-release tablets in Healthy Male and Female Volunteers/Fasting State Objectives:

The primary objective of this study was to compare the relative bioavailability and peak and trough concentrations between two FDA approved regimens of commercially available ondansetron 8 mg immediate-release tablet (twice daily Zofran® 8 mg regimen administered for two days and a single dose of Zofran® 24 mg regimen administered as three Zofran® 8 mg tablets taken together) and the Test Product of ondansetron 24 mg extended-release tablet of the present invention (administered once daily).

Secondary objectives of the study were:
1. To assess the accumulation of ondansetron in the plasma after dosing with the Test Product for five consecutive daily doses, under fasting conditions
2. To assess the safety and tolerability of the extended-release formulation on healthy volunteers.

Methodology:

Single center, randomized, open-label, 3-period, 3-sequence, crossover design.

Number of Subjects (Planned and Analyzed):

Planned for inclusion: 18
Included: 18
Drop-outs: 0
Analyzed: 18
Considered in the pharmacokinetic and statistical analysis: 18
Considered in the safety analysis: 18

Diagnosis and Main Criteria of Inclusion:

Male and female volunteers, non- or ex-smokers, of at least 18 years of age with a body mass index greater than or equal to 18.50 and below 30.00 kg/m$^2$ were included in the study. Subjects were in good health as determined by a medical history, complete physical examination (including vital signs), 12-lead Electrocardiogram (ECG) and the usual clinical laboratory tests (general biochemistry, hematology, urinalysis) including negative Human Immunodeficiency Virus (HIV), Hepatitis B and Hepatitis C tests as well as negative urine drug screening of alcohol, cotinine and drugs of abuse and negative beta Human Chorionic Gonadotropin (HCG) qualitative serum pregnancy test (for female subjects).

Test Product, Dose and Mode of Administration:
Name: Ondansetron
Dosage form/Route of administration: A bimodal tablet of the present invention (Electrolyte CDT Core)/Oral ("Test Product")
Regimen for Treatment-1: Single 24 mg dose (1×24 mg) once daily for 5 consecutive days
Reference Product, Dose and Mode of Administration:
Name: Zofran®
Dosage form/Route of administration: Tablet/Oral
Regimen for Treatment-2: Single 8 mg dose (1×8 mg) twice daily at an 8-hour interval on Day 1 and at a 12-hour interval on Day 2
Regimen for Treatment-3: Single 24 mg dose (3×8 mg)
Treatments:
Treatment-1: Test administered once daily for 5 consecutive days
Treatment-2: Reference administered twice daily, at 8-hour intervals on Day 1 and at 12-hour intervals on Day 2
Treatment-3: A single 24 mg dose administered as three Reference tablets taken together
Treatment Periods:
Period 1: 2013/08/08 to 2013/08/12 (Treatment-1)
Period 1: 2013/08/08 to 2013/08/09 (Treatment-2)
Period 1: 2013/08/08 (Treatment-3)
Period 2: 2013/08/17 to 2013/08/21 (Treatment-1)
Period 2: 2013/08/17 to 2013/08/18 (Treatment-2)
Period 2: 2013/08/17 (Treatment-3)
Period 3: 2013/08/26 to 2013/08/30 (Treatment-1)
Period 3: 2013/08/26 to 2013/08/27 (Treatment-2)
Period 3: 2013/08/26 (Treatment-3)
Duration of Treatment:
Treatment-1: A single 24 mg dose of ondansetron (1×24 mg bimodal tablet (Electrolyte CDT Core)) ("Test Product") was orally administered once daily in the morning following a 10-hour overnight fast for 5 consecutive days.
Treatment-2: A single 8 mg dose of Zofran® (1×8 mg tablet) was orally administered twice daily, for two consecutive days, at 8-hour intervals on Day 1 and at 12-hour intervals on Day 2 (first dose in the morning of each day following a 10-hour overnight fast, and a second dose in the afternoon (Day 1) or evening (Day 2)) (for a total of 4 drug administrations).
Treatment-3: A single 24 mg dose of Zofran® (3×8 mg tablets) was orally administered following a 10-hour overnight fast.

The wash-out period between the first drug administrations of each study period was to be of 9 calendar days.

Blood Sampling Points:
During the study, a total of 98 blood samples were collected as follows:
Treatment-1: On Days 1 and 2 of dosing, 13 blood samples were collected per day. The first blood sample was collected prior to drug administration (within 5 minutes) while the others were collected 1, 2, 3, 4, 5, 6, 8, 10, 12, 14, 16 and 20 hours post drug administration.
On Days 3 and 4 of dosing, 8 blood samples were collected per day, the first blood sample was collected prior to drug administration (within 5 minutes) while the others were collected 2, 4, 6, 8, 10, 14 and 18 hours post drug administration.
On Day 5 of dosing, 10 blood samples were collected, the first blood sample was collected prior to drug administration (within 5 minutes) while the others were collected 2, 4, 6, 8, 10, 14, 18, 24 and 48 hours post drug administration.
For a total of 52 samples per subject with this treatment.
Treatment-2: On Day 1 of dosing, 15 blood samples were collected. The first blood sample was collected prior to the morning drug administration (within 5 minutes) while the others were collected 1, 2, 3, 4, 5, 6, 8, 9, 10, 11, 12, 14, 16, and 20 hours following the morning drug administration. The 8-hour blood sample was collected within 5 minutes before the afternoon administration.
On Day 2 of dosing, 17 blood samples were collected. The first blood sample was collected prior to the morning drug administration (within 5 minutes) while the others were collected 1, 2, 3, 4, 5, 6, 8, 12, 13, 14, 15, 16, 18, 20, 24 and 48 hours following the morning drug administration. The 12-hour blood sample was collected within 5 minutes before the evening administration.
For a total of 32 samples per subject with this treatment.
Treatment-3: On Day 1 of dosing, 14 blood samples were collected. The first blood sample was collected prior to the drug administration (within 5 minutes) while the others were collected 1, 2, 3, 4, 5, 6, 8, 10, 12, 16, 20, 24 and 48 hours following drug administration.

Criteria for Evaluation
Analytical Method:
Analyte: Ondansetron in human plasma
Method: HPLC with MS/MS detection
Assay range: 0.500 ng/mL to 300.000 ng/mL
Safety:
Safety was evaluated through assessment of adverse events, standard laboratory evaluations, vital signs, ECG and physical examination.

Mathematical Model and Statistical Methods of Pharmacokinetic Parameters

Main absorption and disposition parameters using a non-compartmental approach with a log-linear terminal phase assumption. Trapezoidal rule to estimate area under the curve, terminal phase estimation based on maximizing the coefficient of determination. The pharmacokinetic parameters of interest for this study were to be $C_{max}$ for each day of dosing, $AUC_{0-24}$ for each day of dosing, $C_{min}$ for each day of dosing and $C_{24}$ for each dosing day. Other parameters including $T_{max}$ for each dosing day, $AUC_T$, $AUC_\infty$, $AUC_{T/\infty}$, $K_{el}$ and $T_{1/2el}$ were to be calculated.

Statistical analysis of all pharmacokinetic parameters based on a parametric random ANOVA model. Two-sided 90% confidence interval of the ratio of geometric LSmeans obtained from the ln-transformed pharmacokinetic parameters.

During treatment with the Test product, $C_{max}$ and $AUC_{0-24}$ on Days 2 through 5 were to be compared with $C_{max}$ and $AUC_{0-24}$ on Day 1 to assess accumulation with repeated dosing.

Accumulation of the Test formulation was to be evaluated using ln-transformed $C_{max}$ and $AUC_{0-24}$. An Analysis of Variance (ANOVA) model was to be fitted with the day as a fixed effect and the subject as a random effect.

ANOVA Model for Treatments Comparisons:
fixed factors: sequence, period, treatment
random factor: subject (nested within sequence)
ANOVA for Accumulation:
fixed factors: day
random factor: subject Standards for Comparative Bioavailability:

Concentrations of ondansetron over time after dosing with the Test formulation were to be compared with those after dosing with the reference regimens. A single 24 mg dose of immediate release ondansetron was considered effective for prevention of nausea and vomiting from highly emetogenic cancer chemotherapy, and twice daily 8 mg dosing was considered effective for moderately emetogenic chemotherapy. Therefore, if the concentration of ondansetron after dosing with Test Product was found to be similar to or higher than that after dosing with one or both of the reference regimens at most time points over the first 24-hour period studied, one can conclude that the Test product was to be at least as effective treatment with the existing regimens for moderately emetogenic cancer chemotherapy.

Safety:

Descriptive statistics.

Summary of Results

Safety Results:

Nine (9) of the 18 subjects (50.0%) included in this study experienced a total of 28 adverse events. All of the 28 adverse events reported during the study were mild in severity. The below table presents the number of adverse events by treatment classified by severity and causality:

TABLE 20

Number of Patients with Adverse Events

| Treatments | Severity | | | Causality | |
|---|---|---|---|---|---|
| | Mild | Moderate | Severe | Reasonable Possibility | No Reasonable Possibility |
| Test Product | 6 | 0 | 0 | 4 | 4 |
| Zofran 8 mg bid | 5 | 0 | 0 | 3 | 3 |
| Zofran 24 mg × 1 | 6 | 0 | 0 | 3 | 3 |
| Total number of patients with adverse events | 9 | 0 | 0 | 7 | 6 |

Six (6) subjects (33.3%) reported 12 adverse events (2 different System Organ Classes and 7 different Preferred Terms) after the administration of Treatment-1, 5 subjects (27.8%) reported 7 adverse events (3 different System Organ Classes and 5 different Preferred Terms) after the administration of Treatment-2 and 6 subjects (33.3%) reported 9 adverse events (4 different System Organ Classes and 7 different Preferred Terms) after the administration of Treatment-3. The number of subjects who experienced at least one adverse event during the study was similar for all 3 treatments.

Adverse events experienced by two or more subjects with any treatment condition were (Treatment-1, Treatment-2, Treatment-3) abnormal feces (2, 0, 0), constipation (2, 0, 1), vessel puncture site haematoma (2, 3, 2), vessel puncture site pain (0, 1, 1), headache (0, 1, 1) and somnolence (0, 1, 1). Furthermore, related adverse events experienced by two or more subjects with any treatment condition were (Treatment-1, Treatment-2, Treatment-3) constipation (2, 0, 1), headache (0, 1, 1) and somnolence (0, 1, 1).

No serious adverse events or deaths were reported during this study. Moreover, no clinically significant laboratory evaluations, vital signs, ECGs or physical examinations were observed during this study.

No adverse events required the use of medications following the first dosing.

No subject was withdrawn from the study for safety reasons.

Pharmacokinetic Results:

Treatment Comparisons:

The main pharmacokinetic parameters ($C_{min}$, $C_{max}$, $C_{24}$ and $AUC_{0-24}$) of each treatment were measured for each dosing day. Comparisons between the first 2 days of administration of Test Product with the 2 days of administration of Zofran 8 mg bid were performed as well as a comparison between the first day of administration of Test Product with the administration of Zofran 24 mg. A summary of the results of these comparisons is presented in FIGS. 7-13 and Tables 21-24.

TABLE 21

Pharmacokinetic Parameters After Administration of Test Product

| | Test Product | | | |
|---|---|---|---|---|
| | DAY 1 | | DAY 2 | |
| PARAMETER | MEAN | C.V. (%) | MEAN | C.V. (%) |
| $C_{max}$ (ng/mL) | 54.0 | 35.3 | 63.7 | 42.4 |
| ln ($C_{max}$) | 3.94 | 8.4 | 4.08 | 9.6 |
| $C_{min}$ (ng/mL) | 10.2 | 66.5 | 13.6 | 60.1 |
| ln ($C_{min}$) | 2.14 | 28.1 | 2.45 | 23.9 |

TABLE 21-continued

Pharmacokinetic Parameters After Administration of Test Product

| | Test Product | | | |
|---|---|---|---|---|
| | DAY 1 | | DAY 2 | |
| PARAMETER | MEAN | C.V. (%) | MEAN | C.V. (%) |
| $C_{24}$ (ng/mL) | 11.5 | 64.0 | 13.7 | 59.0 |
| ln ($C_{24}$) | 2.27 | 26.4 | 2.46 | 23.2 |
| $AUC_{0-24}$ (ng*h/mL) | 637.6 | 38.6 | 796.8 | 46.6 |
| ln ($AUC_{0-24}$) | 6.389 | 5.9 | 6.589 | 6.5 |

TABLE 22

Pharmacokinetic Parameters After Administration of Zofran 8 mg bid

| | Zofran 8 mg bid | | | |
|---|---|---|---|---|
| | DAY 1 | | DAY 2 | |
| PARAMETER | MEAN | C.V. (%) | MEAN | C.V. (%) |
| $C_{max}$ (ng/mL) | 46.0 | 38.7 | 46.6 | 45.6 |
| ln ($C_{max}$) | 3.77 | 9.0 | 3.76 | 11.1 |
| $C_{min}$ (ng/mL) | 8.72 | 73.2 | 11.6 | 69.3 |
| ln ($C_{min}$) | 1.95 | 34.5 | 2.26 | 27.1 |
| $C_{24}$ (ng/mL) | 8.72 | 73.2 | 13.6 | 68.5 |

TABLE 22-continued

Pharmacokinetic Parameters After Administration of Zofran 8 mg bid

| | Zofran 8 mg bid | | | |
|---|---|---|---|---|
| | DAY 1 | | DAY 2 | |
| PARAMETER | MEAN | C.V. (%) | MEAN | C.V. (%) |
| ln ($C_{24}$) | 1.95 | 34.5 | 2.42 | 26.0 |
| $AUC_{0-24}$ (ng*h/mL) | 539.5 | 43.2 | 606.9 | 49.4 |
| ln ($AUC_{0-24}$) | 6.211 | 6.5 | 6.306 | 7.2 |

TABLE 23

Pharmacokinetic Parameters After Administration of Zofran 24 mg × 1

| | Zofran 24 mg × 1 DAY 1 | |
|---|---|---|
| PARAMETER | MEAN | C.V. (%) |
| $C_{max}$ (ng/mL) | 140 | 31.5 |
| ln ($C_{max}$) | 4.90 | 6.0 |
| $C_{min}$ (ng/mL) | 8.07 | 68.9 |
| ln ($C_{min}$) | 1.90 | 33.0 |
| $C_{24}$ (ng/mL) | 8.07 | 68.9 |
| ln ($C_{24}$) | 1.90 | 33.0 |
| $AUC_{0-24}$ (ng*h/mL) | 1058 | 34.4 |
| ln ($AUC_{0-24}$) | 6.913 | 4.6 |

Concentration Comparisons:

Concentrations of ondansetron at selected time points after dosing with Test Product were compared with those after dosing with Zofran 8 mg bid and Zofran 24 mg×1. Measured concentrations achieved with Test Product at 10, 12 14 and 16 hours post-dose for Day 1 and at 20 hours post-dose for Day 2 were compared to the respective measured concentrations of ondansetron achieved with the administration of the other treatments. A summary of the results of these comparisons is presented in the following tables.

TABLE 25

Concentration After Administration of Test Product

| | | Test Product | |
|---|---|---|---|
| PARAMETER | DAY | MEAN | C.V. (%) |
| $C_{10}$ (ng/mL) | 1 | 30.2 | 40.3 |
| ln ($C_{10}$) | 1 | 3.33 | 13.0 |
| $C_{12}$ (ng/mL) | 1 | 25.0 | 42.8 |
| ln ($C_{12}$) | 1 | 3.14 | 13.4 |
| $C_{14}$ (ng/mL) | 1 | 20.7 | 48.1 |
| ln ($C_{14}$) | 1 | 2.93 | 15.4 |
| $C_{16}$ (ng/mL) | 1 | 17.7 | 51.9 |
| ln ($C_{16}$) | 1 | 2.76 | 17.8 |
| $C_{20}$ (ng/mL) | 1 | 12.8 | 57.9 |
| ln ($C_{20}$) | 1 | 2.41 | 22.3 |

N/AP: Not applicable

TABLE 24

Treatment Comparisons (Continued)

| Comparison | DAY | INTRA-SUBJECT C.V. (%) | GEOMETRIC LSMEANS* Test Product | GEOMETRIC LSMEANS* TREATMENT** | RATIO (%) | 90% CONFIDENCE LIMITS (%) LOWER | 90% CONFIDENCE LIMITS (%) UPPER |
|---|---|---|---|---|---|---|---|
| $C_{max}$ | | | | | | | |
| Test Product vs Zofran 8 mg bid | 1 | 13.6 | 51.2 | 43.3 | 118 | 109 | 128 |
| Test Product vs Zofran 24 mg × 1 | 1 | 13.6 | 51.2 | 135 | 38.1 | 35.3 | 41.1 |
| Test Product vs Zofran 8 mg bid | 2 | 11.1 | 59.0 | 42.7 | 138 | 130 | 147 |
| $C_{min}$ | | | | | | | |
| Test Product vs Zofran 8 mg bid | 1 | 28.1 | 8.50 | 7.04 | 121 | 103 | 141 |
| Test Product vs Zofran 24 mg × 1 | 1 | 28.1 | 8.50 | 6.69 | 127 | 109 | 148 |
| Test Product vs Zofran 8 mg bid | 2 | 22.7 | 11.5 | 9.61 | 120 | 105 | 137 |
| $C_{24}$ | | | | | | | |
| Test Product vs Zofran 8 mg bid | 1 | 26.6 | 9.69 | 7.04 | 138 | 119 | 160 |
| Test Product vs Zofran 24 mg × 1 | 1 | 26.6 | 9.69 | 6.69 | 145 | 125 | 168 |
| Test Product vs Zofran 8 mg bid | 2 | 23.8 | 11.7 | 11.3 | 104 | 90.9 | 120 |
| $AUC_{0-24}$ | | | | | | | |
| Test Product vs Zofran 8 mg bid | 1 | 12.2 | 595.4 | 498.4 | 119.5 | 111.6 | 127.9 |
| Test Product vs Zofran 24 mg × 1 | 1 | 12.2 | 595.4 | 1005 | 59.22 | 55.30 | 63.42 |
| Test Product vs Zofran 8 mg bid | 2 | 12.4 | 726.9 | 547.9 | 132.7 | 123.5 | 142.6 |

*Units are ng/mL for $C_{max}$, $C_{min}$ and $C_{24}$ and ng * h/mL for $AUC_{0-24}$
**Refers to Zofran 8 mg bid or Zofran 24 mg × 1 according to the comparison

TABLE 26

Concentration After Administration of Zofran 8 mg bid

| PARAMETER | DAY | Zofran 8 mg bid MEAN | C.V. (%) |
|---|---|---|---|
| $C_{10}$ (ng/mL) | 1 | 44.7 | 37.4 |
| $\ln(C_{10})$ | 1 | 3.74 | 8.9 |
| $C_{12}$ (ng/mL) | 1 | 32.9 | 44.1 |
| $\ln(C_{12})$ | 1 | 3.41 | 12.2 |
| $C_{14}$ (ng/mL) | 1 | 24.1 | 48.2 |
| $\ln(C_{14})$ | 1 | 3.08 | 15.5 |
| $C_{16}$ (ng/mL) | 1 | 19.2 | 56.7 |
| $\ln(C_{16})$ | 1 | 2.82 | 18.8 |
| $C_{20}$ (ng/mL) | 1 | 12.2 | 63.1 |
| $\ln(C_{20})$ | 1 | 2.33 | 26.3 |

TABLE 27

Concentration After Administration of Zofran 24 mg × 1

| PARAMETER | DAY | Zofran 24 mg × 1 MEAN | C.V. (%) |
|---|---|---|---|
| $C_{10}$ (ng/mL) | 1 | 37.9 | 40.1 |
| $\ln(C_{10})$ | 1 | 3.56 | 11.4 |
| $C_{12}$ (ng/mL) | 1 | 27.4 | 44.2 |
| $\ln(C_{12})$ | 1 | 3.22 | 13.4 |
| $C_{14}$ (ng/mL) | 1 | N/AP | N/AP |
| $\ln(C_{14})$ | 1 | N/AP | N/AP |
| $C_{16}$ (ng/mL) | 1 | 16.0 | 54.8 |
| $\ln(C_{16})$ | 1 | 2.64 | 19.6 |
| $C_{20}$ (ng/mL) | 1 | 10.8 | 60.6 |
| $\ln(C_{20})$ | 1 | 2.23 | 25.5 |

TABLE 28

Concentration Comparisons After Administration

| Comparison | Parameter | Day | INTRA-SUBJECT C.V. (%) | GEOMETRIC LSMEANS (ng/mL) Test Product | TREATMENT* | RATIO (%) | 90% CONFIDENCE LIMITS (%) LOWER | UPPER |
|---|---|---|---|---|---|---|---|---|
| Test Product vs Zofran 8 mg bid | $C_{10}$ | 1 | 18.9 | 27.8 | 42.3 | 65.8 | 59.2 | 73.1 |
| Test Product vs Zofran 24 mg × 1 | $C_{10}$ | 1 | 18.9 | 27.8 | 35.1 | 79.2 | 71.3 | 88.0 |
| Test Product vs Zofran 8 mg bid | $C_{12}$ | 1 | 16.9 | 23.0 | 30.3 | 76.0 | 69.1 | 83.5 |
| Test Product vs Zofran 24 mg × 1 | $C_{12}$ | 1 | 16.9 | 23.0 | 25.1 | 91.5 | 83.2 | 101 |
| Test Product vs Zofran 8 mg bid | $C_{14}$ | 1 | 21.7 | 18.7 | 21.7 | 86.4 | 76.2 | 98.0 |
| Test Product vs Zofran 8 mg bid | $C_{16}$ | 1 | 18.9 | 15.7 | 16.8 | 93.7 | 84.2 | 104 |
| Test Product vs Zofran 24 mg × 1 | $C_{16}$ | 1 | 18.9 | 15.7 | 14.1 | 112 | 101 | 124 |
| Test Product vs Zofran 8 mg bid | $C_{20}$ | 1 | 22.6 | 11.1 | 10.3 | 108 | 95.5 | 123 |
| Test Product vs Zofran 24 mg × 1 | $C_{20}$ | 1 | 22.6 | 11.1 | 9.28 | 120 | 106 | 136 |

*Refers to Zofran 8 mg bid or Zofran 24 mg × 1 according to the comparison

Accumulation Evaluation:

In order to evaluate the accumulation of ondansetron after multiple administrations of Test Product, $C_{max}$ and $AUC_{0-24}$ were measured for 5 consecutive days of dosing and compared to the single dose administration of Test Product at Day 1. A summary of the results is presented in the following tables.

TABLE 29

Accumulation Evaluation of Test Product - $C_{max}$

| Comparison | INTRA-SUBJECT C.V. (%) | GEOMETRIC LSMEANS (ng/mL) DAY* | DAY 1 | RATIO (%) | 90% CONFIDENCE LIMITS (%) LOWER | UPPER |
|---|---|---|---|---|---|---|
| Day 2 vs Day 1 | 8.8 | 59.0 | 51.2 | 115 | 110 | 121 |
| Day 3 vs Day 1 | 8.8 | 60.6 | 51.2 | 118 | 113 | 124 |
| Day 4 vs Day 1 | 8.8 | 62.7 | 51.2 | 122 | 117 | 129 |
| Day 5 vs Day 1 | 8.8 | 64.1 | 51.2 | 125 | 119 | 131 |

*Refers to Day 2, 3, 4 or 5 according to the comparison

TABLE 30

Accumulation Evaluation of Test Product - $AUC_{0-24}$

| Comparison | INTRA-SUBJECT C.V. (%) | GEOMETRIC LSMEANS (ng * h/mL) | | RATIO (%) | 90% CONFIDENCE LIMITS (%) | |
|---|---|---|---|---|---|---|
| | | DAY* | DAY 1 | | LOWER | UPPER |
| Day 2 vs Day 1 | 9.1 | 726.9 | 595.4 | 122.1 | 116.1 | 128.4 |
| Day 3 vs Day 1 | 9.1 | 743.8 | 595.4 | 125.0 | 118.8 | 131.4 |
| Day 4 vs Day 1 | 9.1 | 781.3 | 595.4 | 131.2 | 124.7 | 138.0 |
| Day 5 vs Day 1 | 9.1 | 784.0 | 595.4 | 131.7 | 125.2 | 138.5 |

*Refers to Day 2, 3, 4 or 5 according to the comparison

Pharmacokinetic Discussion:
Treatment Comparisons:
Test Product vs Zofran 8 mg Bid:

The results presented herein show that the $C_{min}$ and $C_{max}$ over 24 hours as well as $AUC_{0-24}$ were higher during the first two days of administration of Test Product as compared to both days of administration of Zofran 8 mg bid.

The $C_{24}$ was found to be higher with the administration of Test Product for the first day of treatment and was found to be comparable between Test Product and Zofran 8 mg bid for the second day of treatment.

Test Product vs Zofran 24 mg×1:

The $C_{min}$ and $C_{24}$ were also higher for the first day of administration of Test Product as compared to the administration of Zofran 24 mg×1.

However, the $C_{max}$ and $AUC_{0-24}$ achieved with the administration of Test Product were about 60% (ratio of 38%) and 40% (ratio of 59%) lower than the $C_{max}$ and $AUC_{0-24}$ achieved with the administration of Zofran 24 mg×1.

Concentration Comparisons:
Test Product vs Zofran 8 mg Bid:

Measured concentrations from 3 through 8 hours after initial dosing were higher after administration of Test Product. At 10 and 12 hours, concentrations were found to be lower with the administration of Test Product for the first day of treatment; subsequent concentrations were similar between the two groups on the first day.

Due to the later administration of the second dose on day 2, the shape of the concentration curve for Zofran 8 mg bid was somewhat different than on the first day, but the overall results were similar.

Test Product vs Zofran 24 mg×1:

Measured concentrations through 10 hours were found to be lower following the administration of Test Product. The measured concentration at 12 and 16 hours were found to be comparable between the two treatments and higher for Test Product at 20 and 24 hours.

Accumulation Evaluation

The accumulation evaluation performed on $C_{max}$ demonstrated a first 15% increase between Day 1 and Day 2 and also demonstrated a uniform increase of the ratio estimate based on back-transformation of LS Means' difference throughout Day 3 to Day 5 (118-125% of $C_{max}$ observed on Day 1) indicating the accumulation of ondansetron following multiple administrations of Test Product. A similar increase was observed for $AUC_{0-24}$ for Day 3 and 4 (125-131% of $AUC_{0-24}$ observed on Day 1) following a 22% increase between Day 1 and Day 2.

The ratio estimate based on back-transformation of LS Means' difference for the $AUC_{0-24}$ was similar for Day 4 (131%) and Day 5 (132%) indicating that steady state had been reached between day 4 and 5 of repeated daily Test Product administration.

Conclusions:
Comparative Bioavailability:

The results presented herein demonstrate that bioavailability of Test Product is noninferior to that of Zofran 8 mg bid, the approved regimen for prevention of nausea and vomiting due to moderately emetogenic chemotherapy.

Key points in this comparison:
Geometric mean $AUC_{0-24}$ of Test Product was 19% higher than that of Zofran 8 mg bid (90% CI 12-28%) on day 1 of dosing, 33% higher (90% CI 24-43%) on day 2.

Geometric mean $C_{max}$ of Test Product was 18% higher than that of Zofran 8 mg bid (90% CI 9-28%) on day 1 of dosing, 38% higher on day 2 (90% CI 30-47%).

Both $C_{24}$ and $C_{min}$ of Test Product were higher than those of both Zofran 8 mg bid and Zofran 24 mg×1

Ondansetron levels were similar to or higher after Test Product than after Zofran 8 mg at all time points except 10 and 12 hours after initial dosing on day 1 and 14-20 hours on day 2.

At 10 and 12 hours after dosing on day 1, the levels after Test Product were 107% and 72% higher than the trough ondansetron level 8 hours after the initial dose of Zofran 8 mg.

At 14-20 hours after initial dosing on day 2, levels after Test Product were 47-159% higher than the trough ondansetron level 12 hours after the initial dose of Zofran 8 mg.

In addition, from 12 hours on, levels of ondansetron after Test Product were similar to or higher than levels after Zofran 24 mg×1, which is the approved regimen for highly emetogenic chemotherapy.

The plasma level of ondansetron after Test Product is similar to or higher than the plasma level after Zofran 8 mg given twice daily at most time points tested, and the concentrations at other time points are considerably higher than trough levels at 8 or 12 hours (days 1 and 2 respectively) after the initial dose for the reference regimen of Zofran 8 mg twice daily. Therefore, it is reasonable to conclude that the efficacy of Test Product is at least as good as that of the Zofran 8 mg twice daily.

Accumulation Assessment:

The once daily administration of Test Product for 5 consecutive days under fasting conditions confirmed an accumulation of ondansetron in human plasma. Maximum plasma concentrations increased from 15% to 25% from Day 2 to Day 5. Following the first 15% increase, an increase of ≈3% of the maximum concentration was observed for each subsequent dosing day. $AUC_{0-24}$ increased from 22 to 31% from Day 2 to Day 4 and subsequently stabilized to 32% for Day 5 indicating arrival at a steady state situation.

Safety and Tolerability of Test Product:

The results presented herein show that the once daily administration of Test Product for 5 consecutive days was safe and well tolerated by the subjects included in this study. Furthermore, the number of subjects who experienced at least one adverse event was comparable between all treatment groups and all of the 28 adverse events reported during the study were mild in severity, demonstrating that the safety and tolerability of the extended-release formulation, Test Product, was similar to the safety profile of the other treatments.

Despite some drug accumulation with repeated dosing, there was no indication that this resulted in any safety issues.

In particular, the incidence of mild QTc prolongation was higher after a single 24 mg dose of immediate release Zofran than it was after 5 daily doses of Test Product.

According to aspects illustrated herein, there is disclosed a solid oral dosage form that includes a core comprising a non-ionic polymer matrix, a first amount of a first antiemetic drug or a pharmaceutically acceptable salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of a second antiemetic drug or a pharmaceutically acceptable salt thereof dispersed therein, wherein the drug layer is sufficiently designed to release the second amount of the antiemetic drug over a period of at least 1 hour, wherein the solid oral dosage form is sufficiently designed to release the first amount of the first antiemetic drug and the second amount of the second antiemetic drug over a minimum period of 16 hours. In an embodiment, the solid oral dosage form further includes an enteric coating surrounding the first seal coat. In an embodiment, the solid oral dosage form further includes a second seal coat surrounding the immediate release drug layer, wherein the second seal coat is comprised of a non-ionic polymer. In an embodiment, the first seal coat further comprises a coating additive such as plasACRYL™. In an embodiment, the salt in the core is dispersed in the matrix at a concentration in the range of 50% to 100% by weight of the matrix. In an embodiment, upon exposure of the solid dosage form to an aqueous medium, the salt causes a hardened boundary around the periphery of the matrix, the boundary sequentially progressing inwardly toward the center thereof as the aqueous medium permeates the matrix, the hardened boundary limiting the rate at which the antiemetic drug in the matrix is released from the tablet. In an embodiment, the solid oral dosage form is sufficiently designed to release the first amount of the antiemetic drug and the second amount of the antiemetic drug over a minimum period of 20 hours. In an embodiment, the solid oral dosage form is sufficiently designed to release the first amount of the antiemetic drug and the second amount of the antiemetic drug over a minimum period of 24 hours. In an embodiment, the first antiemetic drug and the second antiemetic drug are the same drug. In an embodiment, the first antiemetic drug and the second antiemetic drug are each ondansetron or an equivalent amount of an ondansetron salt thereof.

According to aspects illustrated herein, there is disclosed a solid oral dosage form that includes a core comprising hypromellose, 18 mg of ondansetron or an equivalent amount of an ondansetron salt thereof, and sodium citrate anhydrous; a first seal coat surrounding the core and comprising hypromellose; and an immediate release drug layer surrounding the first seal coat and comprising hypromellose and 6 mg of ondansetron or an equivalent amount of an ondansetron salt thereof, the immediate release drug layer sufficient to release the ondansetron over a period of at least 1 hour, wherein the total amount of ondansetron in the dosage form is released over 24 hours. In an embodiment, the solid oral dosage form further includes an enteric coating surrounding the first seal coat. In an embodiment, the solid oral dosage form further includes a second seal coat surrounding the immediate release drug layer, wherein the second seal coat is comprised of a non-ionic polymer. In an embodiment, the first seal coat further comprises a coating additive such as plasACRYL™. In an embodiment, the sodium citrate anhydrous in the core is dispersed in the hypromellose at a concentration in the range of 50% to 100% by weight of the hypromellose. In an embodiment, upon exposure of the solid oral dosage form to an aqueous medium, the sodium citrate anhydrous causes a hardened boundary around the periphery of the hypromellose, the boundary sequentially progressing inwardly toward the center thereof as the aqueous medium permeates the hypromellose, the hardened boundary limiting the rate at which the ondansetron in the hypromellose is released from the tablet. In an embodiment, when the solid oral dosage form is administered to a patient in a fasting state, achieves a $C_{max}$ of at least 50 ng/ml. In an embodiment, when the solid oral dosage form is administered to a patient in a fasting state, achieves AUC of at least 600 nghr/ml.

According to aspects illustrated herein, there is disclosed a solid oral dosage form that includes a core comprising a non-ionic polymer matrix, a first amount of ondansetron or an equivalent amount of an ondansetron salt thereof dispersed within the matrix, and a salt dispersed within the matrix; a first seal coat surrounding the core, wherein the first seal coat is comprised of a non-ionic polymer matrix; and an immediate release drug layer surrounding the first seal coat, wherein the immediate release drug layer comprises a non-ionic polymer and a second amount of ondansetron or an equivalent amount of an ondansetron salt thereof dispersed therein, wherein the solid oral dosage form results in an in vitro ondansetron dissolution profile when measured in a type 2 paddle dissolution apparatus at 37° C. in aqueous solution containing distilled water at 50 rpm that exhibits: a) from about 20% to 50% of the total ondansetron is released after two and a half hours of measurement in the apparatus; b) from about 50% to 70% of the total ondansetron is released after five hours of measurement in the apparatus; and c) no less than about 90% of the total ondansetron is released after fifteen hours of measurement in the apparatus. In an embodiment, when the solid oral dosage form is administered to a patient in a fasting state at a dose of 24 mg ondansetron, achieves a $C_{max}$ of at least 50 ng/ml. In an embodiment, when the solid oral dosage form is administered to a patient in a fasting state at to dose of 24 mg ondansetron, achieves AUC of at least 600 nghr/ml.

According to aspects illustrated herein, there is disclosed a packaged pharmaceutical preparation that includes a plurality of any of the solid oral dosage forms of the present invention in a sealed container and instructions for administering the dosage forms orally to effect prevention of nausea and vomiting According to aspects illustrated herein, there is disclosed a pharmaceutical preparation that includes a plurality of any of the solid oral dosage forms of the present invention each in a discrete sealed housing, and instructions for administering the dosage forms orally to effect prevention of nausea and vomiting.

According to aspects illustrated herein, there is disclosed a unit dosage form for oral administration to a patient, wherein the unit dosage form is sufficiently designed for preventing nausea and vomiting in the patient, and wherein the unit dosage form includes a combination of an immediate release ondansetron component containing a unit dosage of ondansetron or a pharmaceutically acceptable salt thereof in the range of 4 mg to 8 mg; and a controlled release ondansetron component containing a unit dosage of ondansetron or a pharmaceutically acceptable salt thereof in the range of 16 mg to 28 mg, the controlled release ondansetron component comprising a non-ionic polymer matrix, the ondansetron within the matrix, and a salt dispersed within the matrix, and wherein the unit dosage form exhibits a maximum plasma concentration (Cmax) at about 2 to about 5 hours (Tmax) after administration and exhibits a comparable Cmax to a non-controlled release ondansetron formulation administered three times per day without decreasing total drug exposure defined by the area under the concentration-time curve (AUC), thereby enabling reduction of concentration-dependent side effects without a decrease in efficacy.

A packaged pharmaceutical preparation that includes a plurality of the unit dosage forms of the present invention can be contained within a sealed container and include instructions for administering the dosage forms orally to effect prevention of nausea and vomiting.

A packaged pharmaceutical preparation that includes a plurality of the unit dosage forms of the present invention can be contained within a discrete sealed housing and include instructions for administering the dosage forms orally to effect prevention of nausea and vomiting.

A method for preventing nausea and vomiting includes the step of administering a therapeutically-effective amount of a solid oral dosage form or a unit dosage form of the present invention to a patient.

According to aspects illustrated herein, there is disclosed a once-a-day composition that includes: (a) a core comprising a non-ionic polymer matrix, a first amount of ondansetron or an equivalent amount of an ondansetron salt dispersed within the matrix, and a salt dispersed within the matrix; (b) a first seal coat surrounding the core, wherein the first seal coat is comprised of a non-ionic polymer matrix; and (c) an immediate release drug layer surrounding the enteric coating, wherein the immediate release drug layer comprises a non-ionic polymer and a second amount of ondansetron or an equivalent amount of an ondansetron salt dispersed therein, wherein the immediate release drug layer is sufficiently designed to release the second amount of ondansetron over a period of at least 1 hour, wherein the immediate release drug layer releases the second amount of ondansetron in the upper gastrointestinal tract of a human patient, wherein the core releases the first amount of ondansetron in the lower gastrointestinal tract of a human patient, wherein the composition is a tablet or capsule that contains 24 to 40 mg of ondansetron or an equivalent amount of an ondansetron salt, and provides an in vivo plasma profile selected from: (a) a mean $C_{max}$ of at least 50.0 ng/ml; (b) a mean $AUC_{0-24}$ of greater than 550.0 nghr/ml; and (c) a mean $T_{max}$ of between approximately 2.0 hours and 5.0 hours. In an embodiment, the once-a-day composition, when administered once-a-day to a human in a fasted state, is bioequivalent to administration to a human in a fasted state, three-times-a-day, a unit dosage form comprising 8 mg ondansetron. In an embodiment, the bioequivalency is established by a 90% Confidence Interval of between 0.80 and 1.25 for both $C_{max}$ and AUC, when administered to a human. In an embodiment, solubility and dissolution characteristics are pH-independent. In an embodiment, the core has a pH-independent dissolution release profile over a pH range of 1.2-6.8. In an embodiment, each of the core and the immediate release drug layer have a pH-independent dissolution release profile over a pH range of 1.2-6.8. In an embodiment, each of the core and the immediate release drug layer are surrounded by a seal coat comprised of a non-ionic polymer which increases hydrophilicity of the composition and as a result the dissolution profile of the composition is pH-independent.

All patents, patent applications, and published references cited herein are hereby incorporated by reference in their entirety. It will be appreciated that several of the above-disclosed and other features and functions, or alternatives thereof, may be desirably combined into many other different systems or application. Various presently unforeseen or unanticipated alternatives, modifications, variations, or improvements therein may be subsequently made by those skilled in the art.

What is claimed is:

1. An ondansetron tablet comprising
   a monolithic core comprising hypromellose, 18 mg of ondansetron or an equivalent amount of an ondansetron salt thereof dispersed within the hypromellose, and sodium citrate anhydrous dispersed within the hypromellose, wherein the sodium citrate anhydrous is present in an amount sufficient to allow it to form a hardened boundary around the periphery of the hypromellose upon exposure to an aqueous medium so as to limit the rate at which the ondansetron or an equivalent amount of an ondansetron salt thereof dispersed within the hypromellose is released from the core;
   a first non-functional seal coat surrounding the core and comprising hypromellose wherein the first non-functional seal coat has the property to not substantially affect the release of the ondansetron from the ondansetron tablet: and wherein the total amount of ondansetron in the ondansetron tablet: and
   an immediate release drug layer surrounding the first seal coat and comprising hypromellose and 6 mg of ondansetron or an equivalent amount of an ondansetron salt thereof, wherein the immediate release drug layer has the property to release the ondansetron over a period of at least 1 hour,
   wherein the ondansetron tablet yields a burst of approximately 25% ondansetron followed by a zero-order sustained release of ondansetron, and wherein the total amount of ondansetron in the ondansetron tablet is released over 24 hours.

2. The ondansetron tablet of claim 1, further comprising an enteric coating surrounding the first non-functional seal coat.

3. The ondansetron tablet of claim 1, further comprising a second non-functional seal coat surrounding the immediate release drug layer, wherein the second non-functional seal coat is comprised of a non-ionic polymer.

4. The ondansetron tablet of claim 1, wherein the first non-functional seal coat further comprises a coating additive.

5. The ondansetron tablet of claim 1, wherein, when the tablet is administered to a patient in a fasting state, achieves a Cmax of at least 40 ng/ml.

6. The ondansetron tablet of claim 1, wherein, when the tablet is administered to a patient in a fasting state, achieves AUC of at least 450 nghr/ml.

7. The ondansetron tablet of claim 1, wherein a blood ondansetron concentration approximately 24 hours after oral administration of ondansetron (Cmin) is at least 6 ng/ml.

8. The ondansetron tablet of claim 1, wherein a ratio of a maximum blood ondansetron concentration (Cmax) to a blood ondansetron concentration after approximately 24 hours from oral administration of ondansetron (Cmin) is between 3 and 7.

9. A packaged pharmaceutical preparation comprising a plurality of the ondansetron tablets of claim 1 in a sealed container and instructions for administering the tablets orally to effect prevention of nausea and vomiting.

10. A packaged pharmaceutical preparation comprising a plurality of the ondansetron tablets of claim 1 each in a discrete sealed housing, and instructions for administering the tablets orally to effect prevention of nausea and vomiting.

* * * * *

UNITED STATES PATENT AND TRADEMARK OFFICE
CERTIFICATE OF CORRECTION

| | | |
|---|---|---|
| PATENT NO. | : 9,636,305 B2 | Page 1 of 1 |
| APPLICATION NO. | : 14/212694 | |
| DATED | : May 2, 2017 | |
| INVENTOR(S) | : Reza Fathi et al. | |

It is certified that error appears in the above-identified patent and that said Letters Patent is hereby corrected as shown below:

In the Claims

Claim 1, at Column 40, Lines 25-26, please delete ": and wherein the total amount of ondansetron in the ondansetron tablet:"
Claim 1, at Column 40, Lines 25, please add ";" after "tablet"

Signed and Sealed this
Tenth Day of October, 2017

Joseph Matal
*Performing the Functions and Duties of the*
*Under Secretary of Commerce for Intellectual Property and*
*Director of the United States Patent and Trademark Office*